US005530197A

United States Patent [19]
Peferoen et al.

[11] Patent Number: 5,530,197
[45] Date of Patent: Jun. 25, 1996

[54] CONTROL OF OSTRINIA

[75] Inventors: Marnix Peferoen; Stefan Jansens, both of Ghent; Peter Denolf, Gentbrugge, all of Belgium

[73] Assignee: Plant Genetic Systems, N.V., Gent, Belgium

[21] Appl. No.: 463,513

[22] Filed: Jun. 5, 1995

Related U.S. Application Data

[62] Division of Ser. No. 377,690, Jan. 25, 1995, which is a continuation of Ser. No. 164,781, Dec. 10, 1993, abandoned, which is a continuation of Ser. No. 938,362, Aug. 31, 1992, abandoned.

[30] Foreign Application Priority Data

Aug. 19, 1992  [EP]  European Pat. Off. ............. 92402307

[51] Int. Cl.$^6$ ............................. A01H 4/00; A01N 63/00
[52] U.S. Cl. ................................ 800/205; 800/DIG. 56; 424/93.21; 424/93.2; 514/12; 435/172.3
[58] Field of Search .............................. 435/172.3, 252.3, 435/252.31; 800/205, DIG. 56; 536/23.71; 424/93.2, 93.21; 514/12

[56] References Cited

U.S. PATENT DOCUMENTS 5,064,648  6/1992  Hickle et al. ......................... 424/93 R

FOREIGN PATENT DOCUMENTS 0358557  3/1990  European Pat. Off. .
92/0969  6/1992  WIPO .

OTHER PUBLICATIONS

*Plant Molecular Biology*, vol. 16, pp. 1035–1050, 1991, Elizabeth E. Murray, et al., "Analysis of Unstable RNA Transcripts of Insecticidal Crystal Protein Genes of *Bacillus thuringiensis* in Transgenic Plants and Electroporated Protoplasts".

*Eur. J. Biochem*, vol. 161, pp. 273–280, 1986, Herman Höfte, et al., "Structural and Functional Analysis of a Cloned Delta Endotoxin of *Bacillus thuringiensis berliner* 1715".

*Biotechnology*, vol. 5, pp. 807–813, May 1987, David A. Fischoff, et al., "Insect Tolerant Transenic Tomato Plants".

*Nucleic Acids Research*, vol. 16, No. 6, 1988, pp. 2723–2724, B. L. Brizzard et al., "Nucleotide Sequence of an Additional Crystal Protein Gene Cloned from *Bacillus thuringiensis* Subsp. *thuringiensis*".

*Applied and Environmental Microbiology*, vol. 57, No. 2, Feb. 1991, pp. 349–358, M. Von Tersch, et al., "Insecticidal Toxins from *Bacillus thuringiensis* subsp. *kenyae*: Gene Cloning and Characterization and Comparison with *B. thuringiensis* subsp. *kurstaki* CrylA(c) Toxins".

*Phytopathology*, vol. 81, No. 6, Jun. 1991, pp. 704–705, Stephen F. Tomasino, et al., "Field Activity of a Clavibacter XYLI Subsp. Cynodontis/*Bacillus thuringiensis* Recombinant Against European Corn Borer".

*Journal of Economic Entomology*, vol. 83, No. 6, Dec. 1990, pp. 2207–2209, Michael McGuire, et al., "Field Evaluation of Granular Starch Formulations of *Bacillus thuringiensis* Against *Ostrinia nubilalis* (Lepidoptera: Pyralidae)".

*Gene*, vol. 36, pp. 289–300, 1985, M. Adang, et al. "Characterized Full–Length and Truncated Plasmid Clones of the Crystal Protein of *Bacillus thruingiensis* subsp. *kurstaki* HD–73 and their Toxicity to *Manduca sexta*".

*Nucleic Acids Research*, vol. 18, No. 18, 1990, F. Dardenne, "Nucleotide Sequence and Deduced Amino Acid Sequence of a crylA(c) Gene Variant from *Bacillus thuringiensis*".

*Nucleic Acids Research*, vol. 16, No. 22, 1988, M. Haider, et al., "Nucleotide Sequence of a *Bacillus thuringiensis aizawai* IC1 Entomocidal Crystal Protein Gene".

*Medical Reviews*, vol. 53, No. 2, pp. 242–255, Jun. 1989, Herman Höfte, et al., "Insecticidal Crystal Proteins of *Bacillus thuringiensis*".

*Journal of Biotechnology*, vol. 6, pp. 307–322, 1985, M. Hefford, et al., "Sequence of a Lepidopteran Toxin Gene of *Bacillus thuringiensis* subsp *kurstaki* NRD–12".

*Gene*, vol. 53, pp. 113–119, 1987, K. Oeda, et al., "Nucleotide Sequence of the Insecticidal Protein Gene of *Bacillus thuringiensis* Strain *aizawai* IPL7 and its High–Level Expression of *Escherichia coli*".

*Nature*, vol. 328, pp. 33–37, Jul. 1987, M. Vaeck, et al., "Transgenic Plants Protected from Insect Attack".

*Biotechnology*, vol. 8, pp. 939–943, Oct. 1990, F. Perlak, et al., "Insect Resistant Cotton Plants".

*Proc. Natl. Acad. Sci. USA*, vol. 88, pp. 3324–3328, Apr. 1991, F. Perlak, et al., "Modification of the Coding Sequence Enhances Plant Expression of Insect Control Protein Genes".

First International Conference on the Molecular Biology of *Bacillus thruingiensis*, Jul. 26–28, 1991.

*Biotechnology*, vol. 7, Dec. 1989, pp. 1265–1268, X. Delannay, et al., "Field Performance of Transgenic Tomato Plants Expressing the *Bacillus thuringinesis* Var. *kurstaki* Insect Control Protein".

*Primary Examiner*—Che S. Chereskin
*Attorney, Agent, or Firm*—Burns, Doane, Swecker & Mathis

[57] ABSTRACT

A method to combat or control *Ostrinia nubilalis* by contacting such insects with a CryIB protein or a combination of a CryIB protein and a CryIAb or CryIAc protein.

13 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 4074 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Bacillus thuringiensis
( B ) STRAIN: entomocidus HD 110

( i x ) FEATURE:
( A ) NAME/KEY: CDS
( B ) LOCATION: 186..3872
( D ) OTHER INFORMATION: /note="PROPERTIES: CryIB is toxic to Ostrinea nubilalis (among others)"

( x i ) SEQUENCE DESCRIPTION: SEQ ID NO:1:

```
AAACTGTGGC TAAGATAAAT GGCCCTAAAT TATGAAGGTA TATGTGCTAA AGTCCAAAAA     60

GCGGGAGGTA ATTCATCAAA AAATTTTACT ATACAATTTT CTTAGGTAAT GCTGTGTTAA    120

AACTAATCAG TGAAGAAAAG TTAAATAGTT GGTAATATAA GCCCAACATA AAAGGAGGAG    180

TTATA TTG ACT TCA AAT AGG AAA AAT GAG AAT GAA ATT ATA AAT GCT        227
      Met Thr Ser Asn Arg Lys Asn Glu Asn Glu Ile Ile Asn Ala
        1               5                  10

GTA TCG AAT CAT TCC GCA CAA ATG GAT CTA TTA CCA GAT GCT CGT ATT      275
Val Ser Asn His Ser Ala Gln Met Asp Leu Leu Pro Asp Ala Arg Ile
 15                  20                  25                  30

GAG GAT AGC TTG TGT ATA GCC GAG GGG AAC AAT ATT GAT CCA TTT GTT      323
Glu Asp Ser Leu Cys Ile Ala Glu Gly Asn Asn Ile Asp Pro Phe Val
                 35                  40                  45

AGC GCA TCA ACA GTC CAA ACG GGT ATT AAC ATA GCT GGT AGA ATA CTA      371
Ser Ala Ser Thr Val Gln Thr Gly Ile Asn Ile Ala Gly Arg Ile Leu
             50                  55                  60

GGC GTA TTG GGC GTA CCG TTT GCT GGA CAA CTA GCT AGT TTT TAT AGT      419
Gly Val Leu Gly Val Pro Phe Ala Gly Gln Leu Ala Ser Phe Tyr Ser
         65                  70                  75

TTT CTT GTT GGT GAA TTA TGG CCC CGC GGC AGA GAT CAG TGG GAA ATT      467
Phe Leu Val Gly Glu Leu Trp Pro Arg Gly Arg Asp Gln Trp Glu Ile
     80                  85                  90

TTC CTA GAA CAT GTC GAA CAA CTT ATA AAT CAA CAA ATA ACA GAA AAT      515
Phe Leu Glu His Val Glu Gln Leu Ile Asn Gln Gln Ile Thr Glu Asn
 95                 100                 105                 110

GCT AGG AAT ACG GCT CTT GCT CGA TTA CAA GGT TTA GGA GAT TCC TTC      563
Ala Arg Asn Thr Ala Leu Ala Arg Leu Gln Gly Leu Gly Asp Ser Phe
                115                 120                 125

AGA GCC TAT CAA CAG TCA CTT GAA GAT TGG CTA GAA AAC CGT GAT GAT      611
Arg Ala Tyr Gln Gln Ser Leu Glu Asp Trp Leu Glu Asn Arg Asp Asp
            130                 135                 140

GCA AGA ACG AGA AGT GTT CTT CAT ACC CAA TAT ATA GCT TTA GAA CTT      659
Ala Arg Thr Arg Ser Val Leu His Thr Gln Tyr Ile Ala Leu Glu Leu
        145                 150                 155
```

| | | | | | | | | | | | | | | | | |
|---|---|---|---|---|---|---|---|---|---|---|---|---|---|---|---|---|
| GAT | TTT | CTT | AAT | GCG | ATG | CCG | CTT | TTC | GCA | ATT | AGA | AAC | CAA | GAA | GTT | 707 |
| Asp | Phe | Leu | Asn | Ala | Met | Pro | Leu | Phe | Ala | Ile | Arg | Asn | Gln | Glu | Val | |
| 160 | | | | | 165 | | | | | 170 | | | | | | |
| CCA | TTA | TTG | ATG | GTA | TAT | GCT | CAA | GCT | GCA | AAT | TTA | CAC | CTA | TTA | TTA | 755 |
| Pro | Leu | Leu | Met | Val | Tyr | Ala | Gln | Ala | Ala | Asn | Leu | His | Leu | Leu | Leu | |
| 175 | | | | | 180 | | | | | 185 | | | | | 190 | |
| TTG | AGA | GAT | GCC | TCT | CTT | TTT | GGT | AGT | GAA | TTT | GGG | CTT | ACA | TCG | CAG | 803 |
| Leu | Arg | Asp | Ala | Ser | Leu | Phe | Gly | Ser | Glu | Phe | Gly | Leu | Thr | Ser | Gln | |
| | | | | 195 | | | | | 200 | | | | | 205 | | |
| GAA | ATT | CAA | CGC | TAT | TAT | GAG | CGC | CAA | GTG | GAA | CGA | ACG | AGA | GAT | TAT | 851 |
| Glu | Ile | Gln | Arg | Tyr | Tyr | Glu | Arg | Gln | Val | Glu | Arg | Thr | Arg | Asp | Tyr | |
| | | | | 210 | | | | | 215 | | | | | 220 | | |
| TCC | GAC | TAT | TGC | GTA | GAA | TGG | TAT | AAT | ACA | GGT | CTA | AAT | AGC | TTG | AGA | 899 |
| Ser | Asp | Tyr | Cys | Val | Glu | Trp | Tyr | Asn | Thr | Gly | Leu | Asn | Ser | Leu | Arg | |
| | | | 225 | | | | | 230 | | | | | 235 | | | |
| GGG | ACA | AAT | GCC | GCA | AGT | TGG | GTA | CGG | TAT | AAT | CAA | TTC | CGT | AGA | GAT | 947 |
| Gly | Thr | Asn | Ala | Ala | Ser | Trp | Val | Arg | Tyr | Asn | Gln | Phe | Arg | Arg | Asp | |
| | 240 | | | | | 245 | | | | | 250 | | | | | |
| CTA | ACG | TTA | GGA | GTA | TTA | GAT | CTA | GTG | GCA | CTA | TTC | CCA | AGC | TAT | GAC | 995 |
| Leu | Thr | Leu | Gly | Val | Leu | Asp | Leu | Val | Ala | Leu | Phe | Pro | Ser | Tyr | Asp | |
| 255 | | | | | 260 | | | | | 265 | | | | | 270 | |
| ACT | CGC | ACT | TAT | CCA | ATA | AAT | ACG | AGT | GCT | CAG | TTA | ACA | AGA | GAA | GTT | 1043 |
| Thr | Arg | Thr | Tyr | Pro | Ile | Asn | Thr | Ser | Ala | Gln | Leu | Thr | Arg | Glu | Val | |
| | | | | 275 | | | | | 280 | | | | | 285 | | |
| TAT | ACA | GAC | GCA | ATT | GGA | GCA | ACA | GGG | GTA | AAT | ATG | GCA | AGT | ATG | AAT | 1091 |
| Tyr | Thr | Asp | Ala | Ile | Gly | Ala | Thr | Gly | Val | Asn | Met | Ala | Ser | Met | Asn | |
| | | | 290 | | | | | 295 | | | | | 300 | | | |
| TGG | TAT | AAT | AAT | AAT | GCA | CCT | TCG | TTC | TCT | GCC | ATA | GAG | GCT | GCG | GCT | 1139 |
| Trp | Tyr | Asn | Asn | Asn | Ala | Pro | Ser | Phe | Ser | Ala | Ile | Glu | Ala | Ala | Ala | |
| | | 305 | | | | | 310 | | | | | 315 | | | | |
| ATC | CGA | AGC | CCG | CAT | CTA | CTT | GAT | TTT | CTA | GAA | CAA | CTT | ACA | ATT | TTT | 1187 |
| Ile | Arg | Ser | Pro | His | Leu | Leu | Asp | Phe | Leu | Glu | Gln | Leu | Thr | Ile | Phe | |
| | 320 | | | | | 325 | | | | | 330 | | | | | |
| AGC | GCT | TCA | TCA | CGA | TGG | AGT | AAT | ACT | AGG | CAT | ATG | ACT | TAT | TGG | CGG | 1235 |
| Ser | Ala | Ser | Ser | Arg | Trp | Ser | Asn | Thr | Arg | His | Met | Thr | Tyr | Trp | Arg | |
| 335 | | | | | 340 | | | | | 345 | | | | | 350 | |
| GGG | CAC | ACG | ATT | CAA | TCT | CGG | CCA | ATA | GGA | GGC | GGA | TTA | AAT | ACC | TCA | 1283 |
| Gly | His | Thr | Ile | Gln | Ser | Arg | Pro | Ile | Gly | Gly | Gly | Leu | Asn | Thr | Ser | |
| | | | | 355 | | | | | 360 | | | | | 365 | | |
| ACG | CAT | GGG | GCT | ACC | AAT | ACT | TCT | ATT | AAT | CCT | GTA | ACA | TTA | CGG | TTC | 1331 |
| Thr | His | Gly | Ala | Thr | Asn | Thr | Ser | Ile | Asn | Pro | Val | Thr | Leu | Arg | Phe | |
| | | | 370 | | | | | 375 | | | | | 380 | | | |
| GCA | TCT | CGA | GAC | GTT | TAT | AGG | ACT | GAA | TCA | TAT | GCA | GGA | GTG | CTT | CTA | 1379 |
| Ala | Ser | Arg | Asp | Val | Tyr | Arg | Thr | Glu | Ser | Tyr | Ala | Gly | Val | Leu | Leu | |
| | | 385 | | | | | 390 | | | | | 395 | | | | |
| TGG | GGA | ATT | TAC | CTT | GAA | CCT | ATT | CAT | GGT | GTC | CCT | ACT | GTT | AGG | TTT | 1427 |
| Trp | Gly | Ile | Tyr | Leu | Glu | Pro | Ile | His | Gly | Val | Pro | Thr | Val | Arg | Phe | |
| | 400 | | | | | 405 | | | | | 410 | | | | | |
| AAT | TTT | ACG | AAC | CCT | CAG | AAT | ATT | TCT | GAT | AGA | GGT | ACC | GCT | AAC | TAT | 1475 |
| Asn | Phe | Thr | Asn | Pro | Gln | Asn | Ile | Ser | Asp | Arg | Gly | Thr | Ala | Asn | Tyr | |
| 415 | | | | | 420 | | | | | 425 | | | | | 430 | |
| AGT | CAA | CCT | TAT | GAG | TCA | CCT | GGG | CTT | CAA | TTA | AAA | GAT | TCA | GAA | ACT | 1523 |
| Ser | Gln | Pro | Tyr | Glu | Ser | Pro | Gly | Leu | Gln | Leu | Lys | Asp | Ser | Glu | Thr | |
| | | | | 435 | | | | | 440 | | | | | 445 | | |
| GAA | TTA | CCA | CCA | GAA | ACA | ACA | GAA | CGA | CCA | AAT | TAT | GAA | TCT | TAC | AGT | 1571 |
| Glu | Leu | Pro | Pro | Glu | Thr | Thr | Glu | Arg | Pro | Asn | Tyr | Glu | Ser | Tyr | Ser | |
| | | | 450 | | | | | 455 | | | | | 460 | | | |
| CAC | AGG | TTA | TCT | CAT | ATA | GGT | ATA | ATT | TTA | CAA | TCC | AGG | GTG | AAT | GTA | 1619 |
| His | Arg | Leu | Ser | His | Ile | Gly | Ile | Ile | Leu | Gln | Ser | Arg | Val | Asn | Val | |
| | | 465 | | | | | 470 | | | | | 475 | | | | |

```
CCG GTA TAT TCT TGG ACG CAT CGT AGT GCA GAT CGT ACG AAT ACG ATT    1667
Pro Val Tyr Ser Trp Thr His Arg Ser Ala Asp Arg Thr Asn Thr Ile
    480                 485                 490

GGA CCA AAT AGA ATC ACC CAA ATC CCA ATG GTA AAA GCA TCC GAA CTT    1715
Gly Pro Asn Arg Ile Thr Gln Ile Pro Met Val Lys Ala Ser Glu Leu
495                 500                 505                 510

CCT CAA GGT ACC ACT GTT GTT AGA GGA CCA GGA TTT ACT GGT GGG GAT    1763
Pro Gln Gly Thr Thr Val Val Arg Gly Pro Gly Phe Thr Gly Gly Asp
                    515                 520                 525

ATT CTT CGA AGA ACG AAT ACT GGT GGA TTT GGA CCG ATA AGA GTA ACT    1811
Ile Leu Arg Arg Thr Asn Thr Gly Gly Phe Gly Pro Ile Arg Val Thr
            530                 535                 540

GTT AAC GGA CCA TTA ACA CAA AGA TAT CGT ATA GGA TTC CGC TAT GCT    1859
Val Asn Gly Pro Leu Thr Gln Arg Tyr Arg Ile Gly Phe Arg Tyr Ala
        545                 550                 555

TCA ACT GTA GAT TTT GAT TTC TTT GTA TCA CGT GGA GGT ACT ACT GTA    1907
Ser Thr Val Asp Phe Asp Phe Phe Val Ser Arg Gly Gly Thr Thr Val
    560                 565                 570

AAT AAT TTT AGA TTC CTA CGT ACA ATG AAC AGT GGA GAC GAA CTA AAA    1955
Asn Asn Phe Arg Phe Leu Arg Thr Met Asn Ser Gly Asp Glu Leu Lys
575                 580                 585                 590

TAC GGA AAT TTT GTG AGA CGT GCT TTT ACT ACA CCT TTT ACT TTT ACA    2003
Tyr Gly Asn Phe Val Arg Arg Ala Phe Thr Thr Pro Phe Thr Phe Thr
                595                 600                 605

CAA ATT CAA GAT ATA ATT CGA ACG TCT ATT CAA GGC CTT AGT GGA AAT    2051
Gln Ile Gln Asp Ile Ile Arg Thr Ser Ile Gln Gly Leu Ser Gly Asn
                    610                 615                 620

GGG GAA GTG TAT ATA GAT AAA ATT GAA ATT ATT CCA GTT ACT GCA ACC    2099
Gly Glu Val Tyr Ile Asp Lys Ile Glu Ile Ile Pro Val Thr Ala Thr
            625                 630                 635

TTC GAA GCA GAA TAT GAT TTA GAA AGA GCG CAA GAG GCG GTG AAT GCT    2147
Phe Glu Ala Glu Tyr Asp Leu Glu Arg Ala Gln Glu Ala Val Asn Ala
        640                 645                 650

CTG TTT ACT AAT ACG AAT CCA AGA AGA TTG AAA ACA GAT GTG ACA GAT    2195
Leu Phe Thr Asn Thr Asn Pro Arg Arg Leu Lys Thr Asp Val Thr Asp
655                 660                 665                 670

TAT CAT ATT GAT CAA GTA TCC AAT TTA GTG GCG TGT TTA TCG GAT GAA    2243
Tyr His Ile Asp Gln Val Ser Asn Leu Val Ala Cys Leu Ser Asp Glu
                675                 680                 685

TTC TGC TTG GAT GAA AAG AGA GAA TTA CTT GAG AAA GTG AAA TAT GCG    2291
Phe Cys Leu Asp Glu Lys Arg Glu Leu Leu Glu Lys Val Lys Tyr Ala
                    690                 695                 700

AAA CGA CTC AGT GAT GAA AGA AAC TTA CTC CAA GAT CCA AAC TTC ACA    2339
Lys Arg Leu Ser Asp Glu Arg Asn Leu Leu Gln Asp Pro Asn Phe Thr
            705                 710                 715

TCC ATC AAT AAG CAA CCA GAC TTC ATA TCT ACT AAT GAG CAA TCG AAT    2387
Ser Ile Asn Lys Gln Pro Asp Phe Ile Ser Thr Asn Glu Gln Ser Asn
        720                 725                 730

TTC ACA TCT ATC CAT GAA CAA TCT GAA CAT GGA TGG TGG GGA AGT GAG    2435
Phe Thr Ser Ile His Glu Gln Ser Glu His Gly Trp Trp Gly Ser Glu
735                 740                 745                 750

AAC ATT ACC ATC CAG GAA GGA AAT GAC GTA TTT AAA GAG AAT TAC GTC    2483
Asn Ile Thr Ile Gln Glu Gly Asn Asp Val Phe Lys Glu Asn Tyr Val
                755                 760                 765

ACA CTA CCG GGT ACT TTT AAT GAG TGT TAT CCG ACG TAT TTA TAT CAA    2531
Thr Leu Pro Gly Thr Phe Asn Glu Cys Tyr Pro Thr Tyr Leu Tyr Gln
                    770                 775                 780

AAA ATA GGG GAG TCG GAA TTA AAA GCT TAT ACT CGC TAC CAA TTA AGA    2579
Lys Ile Gly Glu Ser Glu Leu Lys Ala Tyr Thr Arg Tyr Gln Leu Arg
            785                 790                 795
```

```
GGT TAT ATT GAA GAT AGT CAA GAT TTA GAG ATA TAT TTG ATT CGT TAT       2627
Gly Tyr Ile Glu Asp Ser Gln Asp Leu Glu Ile Tyr Leu Ile Arg Tyr
    800             805             810

AAT GCG AAA CAT GAA ACA TTG GAT GTT CCA GGT ACC GAG TCC CTA TGG       2675
Asn Ala Lys His Glu Thr Leu Asp Val Pro Gly Thr Glu Ser Leu Trp
815             820             825             830

CCG CTT TCA GTT GAA AGC CCA ATC GGA AGG TGC GGA GAA CCG AAT CGA       2723
Pro Leu Ser Val Glu Ser Pro Ile Gly Arg Cys Gly Glu Pro Asn Arg
                835             840             845

TGC GCA CCA CAT TTT GAA TGG AAT CCT GAT CTA GAT TGT TCC TGC AGA       2771
Cys Ala Pro His Phe Glu Trp Asn Pro Asp Leu Asp Cys Ser Cys Arg
            850             855             860

GAT GGA GAA AAA TGT GCG CAT CAT TCC CAT CAT TTC TCT TTG GAT ATT       2819
Asp Gly Glu Lys Cys Ala His His Ser His His Phe Ser Leu Asp Ile
        865             870             875

GAT GTT GGA TGC ACA GAC TTG CAT GAG AAT CTA GGC GTG TGG GTG GTA       2867
Asp Val Gly Cys Thr Asp Leu His Glu Asn Leu Gly Val Trp Val Val
    880             885             890

TTC AAG ATT AAG ACG CAG GAA GGT CAT GCA AGA CTA GGG AAT CTG GAA       2915
Phe Lys Ile Lys Thr Gln Glu Gly His Ala Arg Leu Gly Asn Leu Glu
895             900             905             910

TTT ATT GAA GAG AAA CCA TTA TTA GGA GAA GCA CTG TCT CGT GTG AAG       2963
Phe Ile Glu Glu Lys Pro Leu Leu Gly Glu Ala Leu Ser Arg Val Lys
                915             920             925

AGG GCA GAG AAA AAA TGG AGA GAC AAA CGT GAA AAA CTA CAA TTG GAA       3011
Arg Ala Glu Lys Lys Trp Arg Asp Lys Arg Glu Lys Leu Gln Leu Glu
            930             935             940

ACA AAA CGA GTA TAT ACA GAG GCA AAA GAA GCT GTG GAT GCT TTA TTC       3059
Thr Lys Arg Val Tyr Thr Glu Ala Lys Glu Ala Val Asp Ala Leu Phe
        945             950             955

GTA GAT TCT CAA TAT GAT AGA TTA CAA GCG GAT ACA AAC ATC GGC ATG       3107
Val Asp Ser Gln Tyr Asp Arg Leu Gln Ala Asp Thr Asn Ile Gly Met
    960             965             970

ATT CAT GCG GCA GAT AAA CTT GTT CAT CGA ATT CGA GAG GCG TAT CTT       3155
Ile His Ala Ala Asp Lys Leu Val His Arg Ile Arg Glu Ala Tyr Leu
975             980             985             990

TCA GAA TTA CCT GTT ATC CCA GGT GTA AAT GCG GAA ATT TTT GAA GAA       3203
Ser Glu Leu Pro Val Ile Pro Gly Val Asn Ala Glu Ile Phe Glu Glu
                995             1000            1005

TTA GAA GGT CAC ATT ATC ACT GCA ATC TCC TTA TAC GAT GCG AGA AAT       3251
Leu Glu Gly His Ile Ile Thr Ala Ile Ser Leu Tyr Asp Ala Arg Asn
            1010            1015            1020

GTC GTT AAA AAT GGT GAT TTT AAT AAT GGA TTA ACA TGT TGG AAT GTA       3299
Val Val Lys Asn Gly Asp Phe Asn Asn Gly Leu Thr Cys Trp Asn Val
        1025            1030            1035

AAA GGG CAT GTA GAT GTA CAA CAG AGC CAT CAT CGT TCT GAC CTT GTT       3347
Lys Gly His Val Asp Val Gln Gln Ser His His Arg Ser Asp Leu Val
    1040            1045            1050

ATC CCA GAA TGG GAA GCA GAA GTG TCA CAA GCA GTT CGC GTC TGT CCG       3395
Ile Pro Glu Trp Glu Ala Glu Val Ser Gln Ala Val Arg Val Cys Pro
1055            1060            1065            1070

GGG TGT GGC TAT ATC CTT CGT GTC ACA GCG TAC AAA GAG GGA TAT GGA       3443
Gly Cys Gly Tyr Ile Leu Arg Val Thr Ala Tyr Lys Glu Gly Tyr Gly
                1075            1080            1085

GAG GGC TGC GTA ACG ATC CAT GAA ATC GAG AAC AAT ACA GAC GAA CTA       3491
Glu Gly Cys Val Thr Ile His Glu Ile Glu Asn Asn Thr Asp Glu Leu
            1090            1095            1100

AAA TTT AAA AAC CGT GAA GAA GAG GAA GTG TAT CCA ACG GAT ACA GGA       3539
Lys Phe Lys Asn Arg Glu Glu Glu Glu Val Tyr Pro Thr Asp Thr Gly
        1105            1110            1115
```

| | | | | | | | | | | | | | | | | |
|---|---|---|---|---|---|---|---|---|---|---|---|---|---|---|---|---|
| ACG | TGT | AAT | GAT | TAT | ACT | GCA | CAC | CAA | GGT | ACA | GCT | GGA | TGC | GCA | GAT | 3587 |
| Thr | Cys | Asn | Asp | Tyr | Thr | Ala | His | Gln | Gly | Thr | Ala | Gly | Cys | Ala | Asp | |
| | 1120 | | | | | 1125 | | | | | 1130 | | | | | |
| GCA | TGT | AAT | TCC | CGT | AAT | GCT | GGA | TAT | GAG | GAT | GCA | TAT | GAA | GTT | GAT | 3635 |
| Ala | Cys | Asn | Ser | Arg | Asn | Ala | Gly | Tyr | Glu | Asp | Ala | Tyr | Glu | Val | Asp | |
| 1135 | | | | | 1140 | | | | | 1145 | | | | | 1150 | |
| ACT | ACA | GCA | TCT | GTT | AAT | TAC | AAA | CCG | ACT | TAT | GAA | GAA | GAA | ACG | TAT | 3683 |
| Thr | Thr | Ala | Ser | Val | Asn | Tyr | Lys | Pro | Thr | Tyr | Glu | Glu | Glu | Thr | Tyr | |
| | | | 1155 | | | | | 1160 | | | | | 1165 | | | |
| ACA | GAT | GTA | AGA | AGA | GAT | AAT | CAT | TGT | GAA | TAT | GAC | AGA | GGG | TAT | GTC | 3731 |
| Thr | Asp | Val | Arg | Arg | Asp | Asn | His | Cys | Glu | Tyr | Asp | Arg | Gly | Tyr | Val | |
| | | | 1170 | | | | | 1175 | | | | | 1180 | | | |
| AAT | TAT | CCA | CCA | GTA | CCA | GCT | GGT | TAT | GTG | ACA | AAA | GAA | TTA | GAA | TAC | 3779 |
| Asn | Tyr | Pro | Pro | Val | Pro | Ala | Gly | Tyr | Val | Thr | Lys | Glu | Leu | Glu | Tyr | |
| | | 1185 | | | | | 1190 | | | | | 1195 | | | | |
| TTC | CCA | GAA | ACA | GAT | ACA | GTA | TGG | ATT | GAG | ATT | GGA | GAA | ACG | GAA | GGA | 3827 |
| Phe | Pro | Glu | Thr | Asp | Thr | Val | Trp | Ile | Glu | Ile | Gly | Glu | Thr | Glu | Gly | |
| | 1200 | | | | | 1205 | | | | | 1210 | | | | | |
| AAG | TTT | ATT | GTA | GAT | AGC | GTG | GAA | TTA | CTC | CTC | ATG | GAA | GAA | TAGGATCATC | | 3879 |
| Lys | Phe | Ile | Val | Asp | Ser | Val | Glu | Leu | Leu | Leu | Met | Glu | Glu | | | |
| 1215 | | | | | 1220 | | | | | 1225 | | | | | | |

| | | | | |
|---|---|---|---|---|
| CAAGTATAGC | AGTTTAATAA | ATATTAATTA | AAATAGTAGT | CTAACTTCCG TTCCAATTAA | 3939 |
| ATAAGTAAAT | TACAGTTGTA | AAAAGAAAAC | GGACATCACT | CTTCAGAGAG CGATGTCCGT | 3999 |
| TTTTTATATG | GTTTGTGCTA | ATGATAAGTG | TGCACGAAAT | TTTATTGTCA AAATAGTATT | 4059 |
| TACTTGAGAA | AAAGA | | | | 4074 |

( 2 ) INFORMATION FOR SEQ ID NO:2:

( i ) SEQUENCE CHARACTERISTICS:
        ( A ) LENGTH: 4343 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Bacillus thuringiensis
        ( B ) STRAIN: berliner 1715

( i x ) FEATURE:
        ( A ) NAME/KEY: CDS
        ( B ) LOCATION: 141..3608
        ( D ) OTHER INFORMATION: /note="coding sequence for CryIAb
            insecticidal crystal protein
            PROPERTIES: CryIAb is toxic to Ostrinia nubilalis
            ( among others )"

( x i ) SEQUENCE DESCRIPTION: SEQ ID NO:2:

| | | | | |
|---|---|---|---|---|
| CAAAAATTGA | TATTTAGTAA | AATTAGTTGC | ACTTTGTGCA | TTTTTTCATA AGATGAGTCA | 60 |
| TATGTTTTAA | ATTGTAGTAA | TGAAAAACAG | TATTATATCA | TAATGAATTG GTATCTTAAT | 120 |

| | | | | | | | | | | | |
|---|---|---|---|---|---|---|---|---|---|---|---|
| AAAAGAGATG | GAGGTAACTT | ATG | GAT | AAC | AAT | CCG | AAC | ATC | AAT | GAA | TGC | 170 |
| | | Met | Asp | Asn | Asn | Pro | Asn | Ile | Asn | Glu | Cys | |
| | | 1 | | | | 5 | | | | | 10 | |

| | | | | | | | | | | | | | | | |
|---|---|---|---|---|---|---|---|---|---|---|---|---|---|---|---|
| ATT | CCT | TAT | AAT | TGT | TTA | AGT | AAC | CCT | GAA | GTA | GAA | GTA | TTA | GGT | GGA | 218 |
| Ile | Pro | Tyr | Asn | Cys | Leu | Ser | Asn | Pro | Glu | Val | Glu | Val | Leu | Gly | Gly | |
| | | | | 15 | | | | | 20 | | | | | 25 | | |
| GAA | AGA | ATA | GAA | ACT | GGT | TAC | ACC | CCA | ATC | GAT | ATT | TCC | TTG | TCG | CTA | 266 |
| Glu | Arg | Ile | Glu | Thr | Gly | Tyr | Thr | Pro | Ile | Asp | Ile | Ser | Leu | Ser | Leu | |
| | | | 30 | | | | | 35 | | | | | 40 | | | |
| ACG | CAA | TTT | CTT | TTG | AGT | GAA | TTT | GTT | CCC | GGT | GCT | GGA | TTT | GTG | TTA | 314 |
| Thr | Gln | Phe | Leu | Leu | Ser | Glu | Phe | Val | Pro | Gly | Ala | Gly | Phe | Val | Leu | |

| | | | | | | | | | | | | | | | | |
|---|---|---|---|---|---|---|---|---|---|---|---|---|---|---|---|---|
| | | | 45 | | | | | | 50 | | | | | 55 | | |
| GGA | CTA | GTT | GAT | ATA | ATA | TGG | GGA | ATT | TTT | GGT | CCC | TCT | CAA | TGG | GAC | 362 |
| Gly | Leu | Val | Asp | Ile | Ile | Trp | Gly | Ile | Phe | Gly | Pro | Ser | Gln | Trp | Asp | |
| | 60 | | | | 65 | | | | | 70 | | | | | | |
| GCA | TTT | CTT | GTA | CAA | ATT | GAA | CAG | TTA | ATT | AAC | CAA | AGA | ATA | GAA | GAA | 410 |
| Ala | Phe | Leu | Val | Gln | Ile | Glu | Gln | Leu | Ile | Asn | Gln | Arg | Ile | Glu | Glu | |
| 75 | | | | | 80 | | | | | 85 | | | | | 90 | |
| TTC | GCT | AGG | AAC | CAA | GCC | ATT | TCT | AGA | TTA | GAA | GGA | CTA | AGC | AAT | CTT | 458 |
| Phe | Ala | Arg | Asn | Gln | Ala | Ile | Ser | Arg | Leu | Glu | Gly | Leu | Ser | Asn | Leu | |
| | | | | 95 | | | | | 100 | | | | | 105 | | |
| TAT | CAA | ATT | TAC | GCA | GAA | TCT | TTT | AGA | GAG | TGG | GAA | GCA | GAT | CCT | ACT | 506 |
| Tyr | Gln | Ile | Tyr | Ala | Glu | Ser | Phe | Arg | Glu | Trp | Glu | Ala | Asp | Pro | Thr | |
| | | | 110 | | | | | 115 | | | | | 120 | | | |
| AAT | CCA | GCA | TTA | AGA | GAA | GAG | ATG | CGT | ATT | CAA | TTC | AAT | GAC | ATG | AAC | 554 |
| Asn | Pro | Ala | Leu | Arg | Glu | Glu | Met | Arg | Ile | Gln | Phe | Asn | Asp | Met | Asn | |
| | | 125 | | | | | 130 | | | | | 135 | | | | |
| AGT | GCC | CTT | ACA | ACC | GCT | ATT | CCT | CTT | TTT | GCA | GTT | CAA | AAT | TAT | CAA | 602 |
| Ser | Ala | Leu | Thr | Thr | Ala | Ile | Pro | Leu | Phe | Ala | Val | Gln | Asn | Tyr | Gln | |
| | 140 | | | | | 145 | | | | | 150 | | | | | |
| GTT | CCT | CTT | TTA | TCA | GTA | TAT | GTT | CAA | GCT | GCA | AAT | TTA | CAT | TTA | TCA | 650 |
| Val | Pro | Leu | Leu | Ser | Val | Tyr | Val | Gln | Ala | Ala | Asn | Leu | His | Leu | Ser | |
| 155 | | | | | 160 | | | | | 165 | | | | | 170 | |
| GTT | TTG | AGA | GAT | GTT | TCA | GTG | TTT | GGA | CAA | AGG | TGG | GGA | TTT | GAT | GCC | 698 |
| Val | Leu | Arg | Asp | Val | Ser | Val | Phe | Gly | Gln | Arg | Trp | Gly | Phe | Asp | Ala | |
| | | | | 175 | | | | | 180 | | | | | 185 | | |
| GCG | ACT | ATC | AAT | AGT | CGT | TAT | AAT | GAT | TTA | ACT | AGG | CTT | ATT | GGC | AAC | 746 |
| Ala | Thr | Ile | Asn | Ser | Arg | Tyr | Asn | Asp | Leu | Thr | Arg | Leu | Ile | Gly | Asn | |
| | | | 190 | | | | | 195 | | | | | 200 | | | |
| TAT | ACA | GAT | CAT | GCT | GTA | CGC | TGG | TAC | AAT | ACG | GGA | TTA | GAG | CGT | GTA | 794 |
| Tyr | Thr | Asp | His | Ala | Val | Arg | Trp | Tyr | Asn | Thr | Gly | Leu | Glu | Arg | Val | |
| | | 205 | | | | | 210 | | | | | 215 | | | | |
| TGG | GGA | CCG | GAT | TCT | AGA | GAT | TGG | ATA | AGA | TAT | AAT | CAA | TTT | AGA | AGA | 842 |
| Trp | Gly | Pro | Asp | Ser | Arg | Asp | Trp | Ile | Arg | Tyr | Asn | Gln | Phe | Arg | Arg | |
| | 220 | | | | | 225 | | | | | 230 | | | | | |
| GAA | TTA | ACA | CTA | ACT | GTA | TTA | GAT | ATC | GTT | TCT | CTA | TTT | CCG | AAC | TAT | 890 |
| Glu | Leu | Thr | Leu | Thr | Val | Leu | Asp | Ile | Val | Ser | Leu | Phe | Pro | Asn | Tyr | |
| 235 | | | | | 240 | | | | | 245 | | | | | 250 | |
| GAT | AGT | AGA | ACG | TAT | CCA | ATT | CGA | ACA | GTT | TCC | CAA | TTA | ACA | AGA | GAA | 938 |
| Asp | Ser | Arg | Thr | Tyr | Pro | Ile | Arg | Thr | Val | Ser | Gln | Leu | Thr | Arg | Glu | |
| | | | | 255 | | | | | 260 | | | | | 265 | | |
| ATT | TAT | ACA | AAC | CCA | GTA | TTA | GAA | AAT | TTT | GAT | GGT | AGT | TTT | CGA | GGC | 986 |
| Ile | Tyr | Thr | Asn | Pro | Val | Leu | Glu | Asn | Phe | Asp | Gly | Ser | Phe | Arg | Gly | |
| | | | 270 | | | | | 275 | | | | | 280 | | | |
| TCG | GCT | CAG | GGC | ATA | GAA | GGA | AGT | ATT | AGG | AGT | CCA | CAT | TTG | ATG | GAT | 1034 |
| Ser | Ala | Gln | Gly | Ile | Glu | Gly | Ser | Ile | Arg | Ser | Pro | His | Leu | Met | Asp | |
| | | 285 | | | | | 290 | | | | | 295 | | | | |
| ATA | CTT | AAC | AGT | ATA | ACC | ATC | TAT | ACG | GAT | GCT | CAT | AGA | GGA | GAA | TAT | 1082 |
| Ile | Leu | Asn | Ser | Ile | Thr | Ile | Tyr | Thr | Asp | Ala | His | Arg | Gly | Glu | Tyr | |
| | 300 | | | | | 305 | | | | | 310 | | | | | |
| TAT | TGG | TCA | GGG | CAT | CAA | ATA | ATG | GCT | TCT | CCT | GTA | GGG | TTT | TCG | GGG | 1130 |
| Tyr | Trp | Ser | Gly | His | Gln | Ile | Met | Ala | Ser | Pro | Val | Gly | Phe | Ser | Gly | |
| 315 | | | | | 320 | | | | | 325 | | | | | 330 | |
| CCA | GAA | TTC | ACT | TTT | CCG | CTA | TAT | GGA | ACT | ATG | GGA | AAT | GCA | GCT | CCA | 1178 |
| Pro | Glu | Phe | Thr | Phe | Pro | Leu | Tyr | Gly | Thr | Met | Gly | Asn | Ala | Ala | Pro | |
| | | | | 335 | | | | | 340 | | | | | 345 | | |
| CAA | CAA | CGT | ATT | GTT | GCT | CAA | CTA | GGT | CAG | GGC | GTG | TAT | AGA | ACA | TTA | 1226 |
| Gln | Gln | Arg | Ile | Val | Ala | Gln | Leu | Gly | Gln | Gly | Val | Tyr | Arg | Thr | Leu | |
| | | | 350 | | | | | 355 | | | | | 360 | | | |
| TCG | TCC | ACT | TTA | TAT | AGA | AGA | CCT | TTT | AAT | ATA | GGG | ATA | AAT | AAT | CAA | 1274 |
| Ser | Ser | Thr | Leu | Tyr | Arg | Arg | Pro | Phe | Asn | Ile | Gly | Ile | Asn | Asn | Gln | |

-continued

|  |  |  |  | 365 |  |  |  | 370 |  |  |  | 375 |  |  |  |  |
|---|---|---|---|---|---|---|---|---|---|---|---|---|---|---|---|---|
| CAA | CTA | TCT | GTT | CTT | GAC | GGG | ACA | GAA | TTT | GCT | TAT | GGA | ACC | TCC | TCA | 1322 |
| Gln | Leu | Ser | Val | Leu | Asp | Gly | Thr | Glu | Phe | Ala | Tyr | Gly | Thr | Ser | Ser |  |
|  | 380 |  |  |  | 385 |  |  |  |  | 390 |  |  |  |  |  |  |
| AAT | TTG | CCA | TCC | GCT | GTA | TAC | AGA | AAA | AGC | GGA | ACG | GTA | GAT | TCG | CTG | 1370 |
| Asn | Leu | Pro | Ser | Ala | Val | Tyr | Arg | Lys | Ser | Gly | Thr | Val | Asp | Ser | Leu |  |
| 395 |  |  |  |  | 400 |  |  |  |  | 405 |  |  |  |  | 410 |  |
| GAT | GAA | ATA | CCG | CCA | CAG | AAT | AAC | AAC | GTG | CCA | CCT | AGG | CAA | GGA | TTT | 1418 |
| Asp | Glu | Ile | Pro | Pro | Gln | Asn | Asn | Asn | Val | Pro | Pro | Arg | Gln | Gly | Phe |  |
|  |  |  |  | 415 |  |  |  |  | 420 |  |  |  |  | 425 |  |  |
| AGT | CAT | CGA | TTA | AGC | CAT | GTT | TCA | ATG | TTT | CGT | TCA | GGC | TTT | AGT | AAT | 1466 |
| Ser | His | Arg | Leu | Ser | His | Val | Ser | Met | Phe | Arg | Ser | Gly | Phe | Ser | Asn |  |
|  |  |  | 430 |  |  |  |  | 435 |  |  |  |  | 440 |  |  |  |
| AGT | AGT | GTA | AGT | ATA | ATA | AGA | GCT | CCT | ATG | TTC | TCT | TGG | ATA | CAT | CGT | 1514 |
| Ser | Ser | Val | Ser | Ile | Ile | Arg | Ala | Pro | Met | Phe | Ser | Trp | Ile | His | Arg |  |
|  |  | 445 |  |  |  |  | 450 |  |  |  |  | 455 |  |  |  |  |
| AGT | GCT | GAA | TTT | AAT | AAT | ATA | ATT | CCT | TCA | TCA | CAA | ATT | ACA | CAA | ATA | 1562 |
| Ser | Ala | Glu | Phe | Asn | Asn | Ile | Ile | Pro | Ser | Ser | Gln | Ile | Thr | Gln | Ile |  |
|  | 460 |  |  |  |  | 465 |  |  |  |  | 470 |  |  |  |  |  |
| CCT | TTA | ACA | AAA | TCT | ACT | AAT | CTT | GGC | TCT | GGA | ACT | TCT | GTC | GTT | AAA | 1610 |
| Pro | Leu | Thr | Lys | Ser | Thr | Asn | Leu | Gly | Ser | Gly | Thr | Ser | Val | Val | Lys |  |
| 475 |  |  |  |  | 480 |  |  |  |  | 485 |  |  |  |  | 490 |  |
| GGA | CCA | GGA | TTT | ACA | GGA | GGA | GAT | ATT | CTT | CGA | AGA | ACT | TCA | CCT | GGC | 1658 |
| Gly | Pro | Gly | Phe | Thr | Gly | Gly | Asp | Ile | Leu | Arg | Arg | Thr | Ser | Pro | Gly |  |
|  |  |  |  | 495 |  |  |  |  | 500 |  |  |  |  | 505 |  |  |
| CAG | ATT | TCA | ACC | TTA | AGA | GTA | AAT | ATT | ACT | GCA | CCA | TTA | TCA | CAA | AGA | 1706 |
| Gln | Ile | Ser | Thr | Leu | Arg | Val | Asn | Ile | Thr | Ala | Pro | Leu | Ser | Gln | Arg |  |
|  |  |  | 510 |  |  |  |  | 515 |  |  |  |  | 520 |  |  |  |
| TAT | CGG | GTA | AGA | ATT | CGC | TAC | GCT | TCT | ACC | ACA | AAT | TTA | CAA | TTC | CAT | 1754 |
| Tyr | Arg | Val | Arg | Ile | Arg | Tyr | Ala | Ser | Thr | Thr | Asn | Leu | Gln | Phe | His |  |
|  |  | 525 |  |  |  |  | 530 |  |  |  |  | 535 |  |  |  |  |
| ACA | TCA | ATT | GAC | GGA | AGA | CCT | ATT | AAT | CAG | GGG | AAT | TTT | TCA | GCA | ACT | 1802 |
| Thr | Ser | Ile | Asp | Gly | Arg | Pro | Ile | Asn | Gln | Gly | Asn | Phe | Ser | Ala | Thr |  |
|  | 540 |  |  |  |  | 545 |  |  |  |  | 550 |  |  |  |  |  |
| ATG | AGT | AGT | GGG | AGT | AAT | TTA | CAG | TCC | GGA | AGC | TTT | AGG | ACT | GTA | GGT | 1850 |
| Met | Ser | Ser | Gly | Ser | Asn | Leu | Gln | Ser | Gly | Ser | Phe | Arg | Thr | Val | Gly |  |
| 555 |  |  |  |  | 560 |  |  |  |  | 565 |  |  |  |  | 570 |  |
| TTT | ACT | ACT | CCG | TTT | AAC | TTT | TCA | AAT | GGA | TCA | AGT | GTA | TTT | ACG | TTA | 1898 |
| Phe | Thr | Thr | Pro | Phe | Asn | Phe | Ser | Asn | Gly | Ser | Ser | Val | Phe | Thr | Leu |  |
|  |  |  |  | 575 |  |  |  |  | 580 |  |  |  |  | 585 |  |  |
| AGT | GCT | CAT | GTC | TTC | AAT | TCA | GGC | AAT | GAA | GTT | TAT | ATA | GAT | CGA | ATT | 1946 |
| Ser | Ala | His | Val | Phe | Asn | Ser | Gly | Asn | Glu | Val | Tyr | Ile | Asp | Arg | Ile |  |
|  |  |  | 590 |  |  |  |  | 595 |  |  |  |  | 600 |  |  |  |
| GAA | TTT | GTT | CCG | GCA | GAA | GTA | ACC | TTT | GAG | GCA | GAA | TAT | GAT | TTA | GAA | 1994 |
| Glu | Phe | Val | Pro | Ala | Glu | Val | Thr | Phe | Glu | Ala | Glu | Tyr | Asp | Leu | Glu |  |
|  |  | 605 |  |  |  |  | 610 |  |  |  |  | 615 |  |  |  |  |
| AGA | GCA | CAA | AAG | GCG | GTG | AAT | GAG | CTG | TTT | ACT | TCT | TCC | AAT | CAA | ATC | 2042 |
| Arg | Ala | Gln | Lys | Ala | Val | Asn | Glu | Leu | Phe | Thr | Ser | Ser | Asn | Gln | Ile |  |
|  | 620 |  |  |  |  | 625 |  |  |  |  | 630 |  |  |  |  |  |
| GGG | TTA | AAA | ACA | GAT | GTG | ACG | GAT | TAT | CAT | ATT | GAT | CAA | GTA | TCC | AAT | 2090 |
| Gly | Leu | Lys | Thr | Asp | Val | Thr | Asp | Tyr | His | Ile | Asp | Gln | Val | Ser | Asn |  |
| 635 |  |  |  |  | 640 |  |  |  |  | 645 |  |  |  |  | 650 |  |
| TTA | GTT | GAG | TGT | TTA | TCT | GAT | GAA | TTT | TGT | CTG | GAT | GAA | AAA | AAA | GAA | 2138 |
| Leu | Val | Glu | Cys | Leu | Ser | Asp | Glu | Phe | Cys | Leu | Asp | Glu | Lys | Lys | Glu |  |
|  |  |  |  | 655 |  |  |  |  | 660 |  |  |  |  | 665 |  |  |
| TTG | TCC | GAG | AAA | GTC | AAA | CAT | GCG | AAG | CGA | CTT | AGT | GAT | GAG | CGG | AAT | 2186 |
| Leu | Ser | Glu | Lys | Val | Lys | His | Ala | Lys | Arg | Leu | Ser | Asp | Glu | Arg | Asn |  |
|  |  |  | 670 |  |  |  |  | 675 |  |  |  |  | 680 |  |  |  |
| TTA | CTT | CAA | GAT | CCA | AAC | TTT | AGA | GGG | ATC | AAT | AGA | CAA | CTA | GAC | CGT | 2234 |
| Leu | Leu | Gln | Asp | Pro | Asn | Phe | Arg | Gly | Ile | Asn | Arg | Gln | Leu | Asp | Arg |  |

|  |  |  |  |  |  |  |  |  |  |  |  |  |  |  |  |
|---|---|---|---|---|---|---|---|---|---|---|---|---|---|---|---|
|  | 685 |  |  |  |  | 690 |  |  |  |  | 695 |  |  |  |  |
| GGC | TGG | AGA | GGA | AGT | ACG | GAT | ATT | ACC | ATC | CAA | GGA | GGC | GAT | GAC | GTA | 2282 |
| Gly | Trp | Arg | Gly | Ser | Thr | Asp | Ile | Thr | Ile | Gln | Gly | Gly | Asp | Asp | Val |  |
| 700 |  |  |  | 705 |  |  |  |  | 710 |  |  |  |  |  |  |  |
| TTC | AAA | GAG | AAT | TAC | GTT | ACG | CTA | TTG | GGT | ACC | TTT | GAT | GAG | TGC | TAC | 2330 |
| Phe | Lys | Glu | Asn | Tyr | Val | Thr | Leu | Leu | Gly | Thr | Phe | Asp | Glu | Cys | Tyr |  |
| 715 |  |  |  | 720 |  |  |  |  | 725 |  |  |  |  | 730 |  |  |
| TTA | ACG | TAT | TTA | TAT | CAA | AAA | ATA | GAT | GAG | TCG | AAA | TTA | AAA | GCC | TAT | 2378 |
| Leu | Thr | Tyr | Leu | Tyr | Gln | Lys | Ile | Asp | Glu | Ser | Lys | Leu | Lys | Ala | Tyr |  |
|  |  |  |  | 735 |  |  |  |  | 740 |  |  |  |  | 745 |  |  |
| ACC | CGT | TAC | CAA | TTA | AGA | GGG | TAT | ATC | GAA | GAT | AGT | CAA | GAC | TTA | GAA | 2426 |
| Thr | Arg | Tyr | Gln | Leu | Arg | Gly | Tyr | Ile | Glu | Asp | Ser | Gln | Asp | Leu | Glu |  |
|  |  |  | 750 |  |  |  |  | 755 |  |  |  |  | 760 |  |  |  |
| ATC | TAT | TTA | ATT | CGC | TAC | AAT | GCC | AAA | CAC | GAA | ACA | GTA | AAT | GTG | CCA | 2474 |
| Ile | Tyr | Leu | Ile | Arg | Tyr | Asn | Ala | Lys | His | Glu | Thr | Val | Asn | Val | Pro |  |
|  |  | 765 |  |  |  |  | 770 |  |  |  |  | 775 |  |  |  |  |
| GGT | ACG | GGT | TCC | TTA | TGG | CGC | CTT | TCA | GCC | CCA | AGT | CCA | ATC | GGA | AAA | 2522 |
| Gly | Thr | Gly | Ser | Leu | Trp | Arg | Leu | Ser | Ala | Pro | Ser | Pro | Ile | Gly | Lys |  |
| 780 |  |  |  |  | 785 |  |  |  |  | 790 |  |  |  |  |  |  |
| TGT | GCC | CAT | CAT | TCC | CAT | CAT | TTC | TCC | TTG | GAC | ATT | GAT | GTT | GGA | TGT | 2570 |
| Cys | Ala | His | His | Ser | His | His | Phe | Ser | Leu | Asp | Ile | Asp | Val | Gly | Cys |  |
| 795 |  |  |  |  | 800 |  |  |  |  | 805 |  |  |  |  | 810 |  |
| ACA | GAC | TTA | AAT | GAG | GAC | TTA | GGT | GTA | TGG | GTG | ATA | TTC | AAG | ATT | AAG | 2618 |
| Thr | Asp | Leu | Asn | Glu | Asp | Leu | Gly | Val | Trp | Val | Ile | Phe | Lys | Ile | Lys |  |
|  |  |  |  | 815 |  |  |  |  | 820 |  |  |  |  | 825 |  |  |
| ACG | CAA | GAT | GGC | CAT | GCA | AGA | CTA | GGA | AAT | CTA | GAA | TTT | CTC | GAA | GAG | 2666 |
| Thr | Gln | Asp | Gly | His | Ala | Arg | Leu | Gly | Asn | Leu | Glu | Phe | Leu | Glu | Glu |  |
|  |  |  | 830 |  |  |  |  | 835 |  |  |  |  | 840 |  |  |  |
| AAA | CCA | TTA | GTA | GGA | GAA | GCA | CTA | GCT | CGT | GTG | AAA | AGA | GCG | GAG | AAA | 2714 |
| Lys | Pro | Leu | Val | Gly | Glu | Ala | Leu | Ala | Arg | Val | Lys | Arg | Ala | Glu | Lys |  |
|  |  | 845 |  |  |  |  | 850 |  |  |  |  | 855 |  |  |  |  |
| AAA | TGG | AGA | GAC | AAA | CGT | GAA | AAA | TTG | GAA | TGG | GAA | ACA | AAT | ATT | GTT | 2762 |
| Lys | Trp | Arg | Asp | Lys | Arg | Glu | Lys | Leu | Glu | Trp | Glu | Thr | Asn | Ile | Val |  |
|  | 860 |  |  |  |  | 865 |  |  |  |  | 870 |  |  |  |  |  |
| TAT | AAA | GAG | GCA | AAA | GAA | TCT | GTA | GAT | GCT | TTA | TTT | GTA | AAC | TCT | CAA | 2810 |
| Tyr | Lys | Glu | Ala | Lys | Glu | Ser | Val | Asp | Ala | Leu | Phe | Val | Asn | Ser | Gln |  |
| 875 |  |  |  |  | 880 |  |  |  |  | 885 |  |  |  |  | 890 |  |
| TAT | GAT | AGA | TTA | CAA | GCG | GAT | ACC | AAC | ATC | GCG | ATG | ATT | CAT | GCG | GCA | 2858 |
| Tyr | Asp | Arg | Leu | Gln | Ala | Asp | Thr | Asn | Ile | Ala | Met | Ile | His | Ala | Ala |  |
|  |  |  |  | 895 |  |  |  |  | 900 |  |  |  |  | 905 |  |  |
| GAT | AAA | CGC | GTT | CAT | AGC | ATT | CGA | GAA | GCT | TAT | CTG | CCT | GAG | CTG | TCT | 2906 |
| Asp | Lys | Arg | Val | His | Ser | Ile | Arg | Glu | Ala | Tyr | Leu | Pro | Glu | Leu | Ser |  |
|  |  |  | 910 |  |  |  |  | 915 |  |  |  |  | 920 |  |  |  |
| GTG | ATT | CCG | GGT | GTC | AAT | GCG | GCT | ATT | TTT | GAA | GAA | TTA | GAA | GGG | CGT | 2954 |
| Val | Ile | Pro | Gly | Val | Asn | Ala | Ala | Ile | Phe | Glu | Glu | Leu | Glu | Gly | Arg |  |
|  |  | 925 |  |  |  |  | 930 |  |  |  |  | 935 |  |  |  |  |
| ATT | TTC | ACT | GCA | TTC | TCC | CTA | TAT | GAT | GCG | AGA | AAT | GTC | ATT | AAA | AAT | 3002 |
| Ile | Phe | Thr | Ala | Phe | Ser | Leu | Tyr | Asp | Ala | Arg | Asn | Val | Ile | Lys | Asn |  |
|  | 940 |  |  |  |  | 945 |  |  |  |  | 950 |  |  |  |  |  |
| GGT | GAT | TTT | AAT | AAT | GGC | TTA | TCC | TGC | TGG | AAC | GTG | AAA | GGG | CAT | GTA | 3050 |
| Gly | Asp | Phe | Asn | Asn | Gly | Leu | Ser | Cys | Trp | Asn | Val | Lys | Gly | His | Val |  |
| 955 |  |  |  |  | 960 |  |  |  |  | 965 |  |  |  |  | 970 |  |
| GAT | GTA | GAA | GAA | CAA | AAC | AAC | CAC | CGT | TCG | GTC | CTT | GTT | GTT | CCG | GAA | 3098 |
| Asp | Val | Glu | Glu | Gln | Asn | Asn | His | Arg | Ser | Val | Leu | Val | Val | Pro | Glu |  |
|  |  |  |  | 975 |  |  |  |  | 980 |  |  |  |  | 985 |  |  |
| TGG | GAA | GCA | GAA | GTG | TCA | CAA | GAA | GTT | CGT | GTC | TGT | CCG | GGT | CGT | GGC | 3146 |
| Trp | Glu | Ala | Glu | Val | Ser | Gln | Glu | Val | Arg | Val | Cys | Pro | Gly | Arg | Gly |  |
|  |  |  | 990 |  |  |  |  | 995 |  |  |  |  | 1000 |  |  |  |
| TAT | ATC | CTT | CGT | GTC | ACA | GCG | TAC | AAG | GAG | GGA | TAT | GGA | GAA | GGT | TGC | 3194 |
| Tyr | Ile | Leu | Arg | Val | Thr | Ala | Tyr | Lys | Glu | Gly | Tyr | Gly | Glu | Gly | Cys |  |

-continued 1005 1010 1015

GTA ACC ATT CAT GAG ATC GAG AAC AAT ACA GAC GAA CTG AAG TTT AGC 3242
Val Thr Ile His Glu Ile Glu Asn Asn Thr Asp Glu Leu Lys Phe Ser
1020 1025 1030

AAC TGT GTA GAA GAG GAA GTA TAT CCA AAC AAC ACG GTA ACG TGT AAT 3290
Asn Cys Val Glu Glu Glu Val Tyr Pro Asn Asn Thr Val Thr Cys Asn
1035 1040 1045 1050

GAT TAT ACT GCG ACT CAA GAA GAA TAT GAG GGT ACG TAC ACT TCT CGT 3338
Asp Tyr Thr Ala Thr Gln Glu Glu Tyr Glu Gly Thr Tyr Thr Ser Arg
1055 1060 1065

AAT CGA GGA TAT GAC GGA GCC TAT GAA AGC AAT TCT TCT GTA CCA GCT 3386
Asn Arg Gly Tyr Asp Gly Ala Tyr Glu Ser Asn Ser Ser Val Pro Ala
1070 1075 1080

GAT TAT GCA TCA GCC TAT GAA GAA AAA GCA TAT ACA GAT GGA CGA AGA 3434
Asp Tyr Ala Ser Ala Tyr Glu Glu Lys Ala Tyr Thr Asp Gly Arg Arg
1085 1090 1095

GAC AAT CCT TGT GAA TCT AAC AGA GGA TAT GGG GAT TAC ACA CCA CTA 3482
Asp Asn Pro Cys Glu Ser Asn Arg Gly Tyr Gly Asp Tyr Thr Pro Leu
1100 1105 1110

CCA GCT GGC TAT GTG ACA AAA GAA TTA GAG TAC TTC CCA GAA ACC GAT 3530
Pro Ala Gly Tyr Val Thr Lys Glu Leu Glu Tyr Phe Pro Glu Thr Asp
1115 1120 1125 1130

AAG GTA TGG ATT GAG ATC GGA GAA ACG GAA GGA ACA TTC ATC GTG GAC 3578
Lys Val Trp Ile Glu Ile Gly Glu Thr Glu Gly Thr Phe Ile Val Asp
1135 1140 1145

AGC GTG GAA TTA CTT CTT ATG GAG GAA TAATATATGC TTTAAAATGT 3625
Ser Val Glu Leu Leu Leu Met Glu Glu
1150 1155

AAGGTGTGCA AATAAAGAAT GATTACTGAC TTGTATTGAC AGATAAATAA GGAAATTTTT 3685

ATATGAATAA AAAACGGGCA TCACTCTTAA AAGAATGATG TCCGTTTTTT GTATGATTTA 3745

ACGAGTGATA TTTAAATGTT TTTTTGCGAA GGCTTTACTT AACGGGGTAC CGCCACATGC 3805

CCATCAACTT AAGAATTTGC ACTACCCCCA AGTGTCAAAA AACGTTATTC TTTCTAAAAA 3865

GCTAGCTAGA AAGGATGACA TTTTTTATGA ATCTTTCAAT TCAAGATGAA TTACAACTAT 3925

TTTCTGAAGA GCTGTATCGT CATTTAACCC CTTCTCTTTT GGAAGAACTC GCTAAAGAAT 3985

TAGGTTTTGT AAAAAGAAAA CGAAAGTTTT CAGGAAATGA ATTAGCTACC ATATGTATCT 4045

GGGTCAGTCA ACGTACAGCG AGTGATTCTC TCGTTCGACT ATGCAGTCAA TTACACGCCG 4105

CCACAGGACC TCTTATGAGT CCAGAAGGAC TCAATAAACG CTTTGATAAA AAAGCGGTTG 4165

AATTTTTGAA ATATATTTTT TCTGCATTAT GGAAAAGTAA ACTTTGTAAA ACATCAGCCA 4225

TTTCAAGTGC AGCACTCACG TATTTTCAAC GAATCCGTAT TTTAGATGCG ACGATTTTCC 4285

AAGTACCGAA ACATTTAGCA CATGTATATC CTGGGTCAGG TGGTTGTGCA CAAACTGC 4343

( 2 ) INFORMATION FOR SEQ ID NO:3:

( i ) SEQUENCE CHARACTERISTICS:
( A ) LENGTH: 3537 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Bacillus thuringiensis
( B ) STRAIN: kurstaki HD-73

( i x ) FEATURE:
( A ) NAME/KEY: CDS
( B ) LOCATION: 1..3537

(D) OTHER INFORMATION: /note="FEATURES: sequence encodes
CryIAc insecticidal crystal protein
PROPERTIES: CryIAc is toxic to Ostrinia nubilalis
(among others)

(xi) SEQUENCE DESCRIPTION: SEQ ID NO:3:

| | | | | | | | | | | | | | | | | |
|---|---|---|---|---|---|---|---|---|---|---|---|---|---|---|---|---|
| ATG | GAT | AAC | AAT | CCG | AAC | ATC | AAT | GAA | TGC | ATT | CCT | TAT | AAT | TGT | TTA | 48 |
| Met | Asp | Asn | Asn | Pro | Asn | Ile | Asn | Glu | Cys | Ile | Pro | Tyr | Asn | Cys | Leu | |
| 1 | | | | 5 | | | | | 10 | | | | | 15 | | |
| AGT | AAC | CCT | GAA | GTA | GAA | GTA | TTA | GGT | GGA | GAA | AGA | ATA | GAA | ACT | GGT | 96 |
| Ser | Asn | Pro | Glu | Val | Glu | Val | Leu | Gly | Gly | Glu | Arg | Ile | Glu | Thr | Gly | |
| | | | 20 | | | | | 25 | | | | | 30 | | | |
| TAC | ACC | CCA | ATC | GAT | ATT | TCC | TTG | TCG | CTA | ACG | CAA | TTT | CTT | TTG | AGT | 144 |
| Tyr | Thr | Pro | Ile | Asp | Ile | Ser | Leu | Ser | Leu | Thr | Gln | Phe | Leu | Leu | Ser | |
| | | 35 | | | | | 40 | | | | | 45 | | | | |
| GAA | TTT | GTT | CCC | GGT | GCT | GGA | TTT | GTG | TTA | GGA | CTA | GTT | GAT | ATA | ATA | 192 |
| Glu | Phe | Val | Pro | Gly | Ala | Gly | Phe | Val | Leu | Gly | Leu | Val | Asp | Ile | Ile | |
| | 50 | | | | | 55 | | | | | 60 | | | | | |
| TGG | GGA | ATT | TTT | GGT | CCC | TCT | CAA | TGG | GAC | GCA | TTT | CTT | GTA | CAA | ATT | 240 |
| Trp | Gly | Ile | Phe | Gly | Pro | Ser | Gln | Trp | Asp | Ala | Phe | Leu | Val | Gln | Ile | |
| 65 | | | | | 70 | | | | | 75 | | | | | 80 | |
| GAA | CAG | TTA | ATT | AAC | CAA | AGA | ATA | GAA | GAA | TTC | GCT | AGG | AAC | CAA | GCC | 288 |
| Glu | Gln | Leu | Ile | Asn | Gln | Arg | Ile | Glu | Glu | Phe | Ala | Arg | Asn | Gln | Ala | |
| | | | | 85 | | | | | 90 | | | | | 95 | | |
| ATT | TCT | AGA | TTA | GAA | GGA | CTA | AGC | AAT | CTT | TAT | CAA | ATT | TAC | GCA | GAA | 336 |
| Ile | Ser | Arg | Leu | Glu | Gly | Leu | Ser | Asn | Leu | Tyr | Gln | Ile | Tyr | Ala | Glu | |
| | | | 100 | | | | | 105 | | | | | 110 | | | |
| TCT | TTT | AGA | GAG | TGG | GAA | GCA | GAT | CCT | ACT | AAT | CCA | GCA | TTA | AGA | GAA | 384 |
| Ser | Phe | Arg | Glu | Trp | Glu | Ala | Asp | Pro | Thr | Asn | Pro | Ala | Leu | Arg | Glu | |
| | | | 115 | | | | | 120 | | | | | 125 | | | |
| GAG | ATG | CGT | ATT | CAA | TTC | AAT | GAC | ATG | AAC | AGT | GCC | CTT | ACA | ACC | GCT | 432 |
| Glu | Met | Arg | Ile | Gln | Phe | Asn | Asp | Met | Asn | Ser | Ala | Leu | Thr | Thr | Ala | |
| | 130 | | | | | 135 | | | | | 140 | | | | | |
| ATT | CCT | CTT | TTT | GCA | GTT | CAA | AAT | TAT | CAA | GTT | CCT | CTT | TTA | TCA | GTA | 480 |
| Ile | Pro | Leu | Phe | Ala | Val | Gln | Asn | Tyr | Gln | Val | Pro | Leu | Leu | Ser | Val | |
| 145 | | | | | 150 | | | | | 155 | | | | | 160 | |
| TAT | GTT | CAA | GCT | GCA | AAT | TTA | CAT | TTA | TCA | GTT | TTG | AGA | GAT | GTT | TCA | 528 |
| Tyr | Val | Gln | Ala | Ala | Asn | Leu | His | Leu | Ser | Val | Leu | Arg | Asp | Val | Ser | |
| | | | | 165 | | | | | 170 | | | | | 175 | | |
| GTG | TTT | GGA | CAA | AGG | TGG | GGA | TTT | GAT | GCC | GCG | ACT | ATC | AAT | AGT | CGT | 576 |
| Val | Phe | Gly | Gln | Arg | Trp | Gly | Phe | Asp | Ala | Ala | Thr | Ile | Asn | Ser | Arg | |
| | | | 180 | | | | | 185 | | | | | 190 | | | |
| TAT | AAT | GAT | TTA | ACT | AGG | CTT | ATT | GGC | AAC | TAT | ACA | GAT | TAT | GCT | GTA | 624 |
| Tyr | Asn | Asp | Leu | Thr | Arg | Leu | Ile | Gly | Asn | Tyr | Thr | Asp | Tyr | Ala | Val | |
| | | 195 | | | | | 200 | | | | | 205 | | | | |
| CGC | TGG | TAC | AAT | ACG | GGA | TTA | GAA | CGT | GTA | TGG | GGA | CCG | GAT | TCT | AGA | 672 |
| Arg | Trp | Tyr | Asn | Thr | Gly | Leu | Glu | Arg | Val | Trp | Gly | Pro | Asp | Ser | Arg | |
| | 210 | | | | | 215 | | | | | 220 | | | | | |
| GAT | TGG | GTA | AGG | TAT | AAT | CAA | TTT | AGA | AGA | GAA | TTA | ACA | CTA | ACT | GTA | 720 |
| Asp | Trp | Val | Arg | Tyr | Asn | Gln | Phe | Arg | Arg | Glu | Leu | Thr | Leu | Thr | Val | |
| 225 | | | | | 230 | | | | | 235 | | | | | 240 | |
| TTA | GAT | ATC | GTT | GCT | CTG | TTC | CCG | AAT | TAT | GAT | AGT | AGA | AGA | TAT | CCA | 768 |
| Leu | Asp | Ile | Val | Ala | Leu | Phe | Pro | Asn | Tyr | Asp | Ser | Arg | Arg | Tyr | Pro | |
| | | | | 245 | | | | | 250 | | | | | 255 | | |
| ATT | CGA | ACA | GTT | TCC | CAA | TTA | ACA | AGA | GAA | ATT | TAT | ACA | AAC | CCA | GTA | 816 |
| Ile | Arg | Thr | Val | Ser | Gln | Leu | Thr | Arg | Glu | Ile | Tyr | Thr | Asn | Pro | Val | |
| | | | 260 | | | | | 265 | | | | | 270 | | | |
| TTA | GAA | AAT | TTT | GAT | GGT | AGT | TTT | CGA | GGC | TCG | GCT | CAG | GGC | ATA | GAA | 864 |
| Leu | Glu | Asn | Phe | Asp | Gly | Ser | Phe | Arg | Gly | Ser | Ala | Gln | Gly | Ile | Glu | |
| | | 275 | | | | | 280 | | | | | 285 | | | | |
| AGA | AGT | ATT | AGG | AGT | CCA | CAT | TTG | ATG | GAT | ATA | CTT | AAC | AGT | ATA | ACC | 912 |

| | | | | | | | | | | | | | | | |
|---|---|---|---|---|---|---|---|---|---|---|---|---|---|---|---|
| Arg | Ser | Ile | Arg | Ser | Pro | His | Leu | Met | Asp | Ile | Leu | Asn | Ser | Ile | Thr |
| | 290 | | | | 295 | | | | | 300 | | | | | |

| | | | | | | | | | | | | | | | | |
|---|---|---|---|---|---|---|---|---|---|---|---|---|---|---|---|---|
| ATC | TAT | ACG | GAT | GCT | CAT | AGG | GGT | TAT | TAT | TAT | TGG | TCA | GGG | CAT | CAA | 960 |
| Ile | Tyr | Thr | Asp | Ala | His | Arg | Gly | Tyr | Tyr | Tyr | Trp | Ser | Gly | His | Gln | |
| 305 | | | | | 310 | | | | | 315 | | | | | 320 | |
| ATA | ATG | GCT | TCT | CCT | GTA | GGG | TTT | TCG | GGG | CCA | GAA | TTC | ACT | TTT | CCG | 1008 |
| Ile | Met | Ala | Ser | Pro | Val | Gly | Phe | Ser | Gly | Pro | Glu | Phe | Thr | Phe | Pro | |
| | | | | 325 | | | | | 330 | | | | | 335 | | |
| CTA | TAT | GGA | ACT | ATG | GGA | AAT | GCA | GCT | CCA | CAA | CAA | CGT | ATT | GTT | GCT | 1056 |
| Leu | Tyr | Gly | Thr | Met | Gly | Asn | Ala | Ala | Pro | Gln | Gln | Arg | Ile | Val | Ala | |
| | | | 340 | | | | | 345 | | | | | 350 | | | |
| CAA | CTA | GGT | CAG | GGC | GTG | TAT | AGA | ACA | TTA | TCG | TCC | ACT | TTA | TAT | AGA | 1104 |
| Gln | Leu | Gly | Gln | Gly | Val | Tyr | Arg | Thr | Leu | Ser | Ser | Thr | Leu | Tyr | Arg | |
| | | 355 | | | | | 360 | | | | | 365 | | | | |
| AGA | CCT | TTT | AAT | ATA | GGG | ATA | AAT | AAT | CAA | CAA | CTA | TCT | GTT | CTT | GAC | 1152 |
| Arg | Pro | Phe | Asn | Ile | Gly | Ile | Asn | Asn | Gln | Gln | Leu | Ser | Val | Leu | Asp | |
| | 370 | | | | | 375 | | | | | 380 | | | | | |
| GGG | ACA | GAA | TTT | GCT | TAT | GGA | ACC | TCC | TCA | AAT | TTG | CCA | TCC | GCT | GTA | 1200 |
| Gly | Thr | Glu | Phe | Ala | Tyr | Gly | Thr | Ser | Ser | Asn | Leu | Pro | Ser | Ala | Val | |
| 385 | | | | | 390 | | | | | 395 | | | | | 400 | |
| TAC | AGA | AAA | AGC | GGA | ACG | GTA | GAT | TCG | CTG | GAT | GAA | ATA | CCG | CCA | CAG | 1248 |
| Tyr | Arg | Lys | Ser | Gly | Thr | Val | Asp | Ser | Leu | Asp | Glu | Ile | Pro | Pro | Gln | |
| | | | | 405 | | | | | 410 | | | | | 415 | | |
| AAT | AAC | AAC | GTG | CCA | CCT | AGG | CAA | GGA | TTT | AGT | CAT | CGA | TTA | AGC | CAT | 1296 |
| Asn | Asn | Asn | Val | Pro | Pro | Arg | Gln | Gly | Phe | Ser | His | Arg | Leu | Ser | His | |
| | | | 420 | | | | | 425 | | | | | 430 | | | |
| GTT | TCA | ATG | TTT | CGT | TCA | GGC | TTT | AGT | AAT | AGT | AGT | GTA | AGT | ATA | ATA | 1344 |
| Val | Ser | Met | Phe | Arg | Ser | Gly | Phe | Ser | Asn | Ser | Ser | Val | Ser | Ile | Ile | |
| | | 435 | | | | | 440 | | | | | 445 | | | | |
| AGA | GCT | CCT | ATG | TTC | TCT | TGG | ATA | CAT | CGT | AGT | GCT | GAA | TTT | AAT | AAT | 1392 |
| Arg | Ala | Pro | Met | Phe | Ser | Trp | Ile | His | Arg | Ser | Ala | Glu | Phe | Asn | Asn | |
| | 450 | | | | | 455 | | | | | 460 | | | | | |
| ATA | ATT | GCA | TCG | GAT | AGT | ATT | ACT | CAA | ATC | CCT | GCA | GTG | AAG | GGA | AAC | 1440 |
| Ile | Ile | Ala | Ser | Asp | Ser | Ile | Thr | Gln | Ile | Pro | Ala | Val | Lys | Gly | Asn | |
| 465 | | | | | 470 | | | | | 475 | | | | | 480 | |
| TTT | CTT | TTT | AAT | GGT | TCT | GTA | ATT | TCA | GGA | CCA | GGA | TTT | ACT | GGT | GGG | 1488 |
| Phe | Leu | Phe | Asn | Gly | Ser | Val | Ile | Ser | Gly | Pro | Gly | Phe | Thr | Gly | Gly | |
| | | | | 485 | | | | | 490 | | | | | 495 | | |
| GAC | TTA | GTT | AGA | TTA | AAT | AGT | AGT | GGA | AAT | AAC | ATT | CAG | AAT | AGA | GGG | 1536 |
| Asp | Leu | Val | Arg | Leu | Asn | Ser | Ser | Gly | Asn | Asn | Ile | Gln | Asn | Arg | Gly | |
| | | | 500 | | | | | 505 | | | | | 510 | | | |
| TAT | ATT | GAA | GTT | CCA | ATT | CAC | TTC | CCA | TCG | ACA | TCT | ACC | AGA | TAT | CGA | 1584 |
| Tyr | Ile | Glu | Val | Pro | Ile | His | Phe | Pro | Ser | Thr | Ser | Thr | Arg | Tyr | Arg | |
| | | 515 | | | | | 520 | | | | | 525 | | | | |
| GTT | CGT | GTA | CGG | TAT | GCT | TCT | GTA | ACC | CCG | ATT | CAC | CTC | AAC | GTT | AAT | 1632 |
| Val | Arg | Val | Arg | Tyr | Ala | Ser | Val | Thr | Pro | Ile | His | Leu | Asn | Val | Asn | |
| | 530 | | | | | 535 | | | | | 540 | | | | | |
| TGG | GGT | AAT | TCA | TCC | ATT | TTT | TCC | AAT | ACA | GTA | CCA | GCT | ACA | GCT | ACG | 1680 |
| Trp | Gly | Asn | Ser | Ser | Ile | Phe | Ser | Asn | Thr | Val | Pro | Ala | Thr | Ala | Thr | |
| 545 | | | | | 550 | | | | | 555 | | | | | 560 | |
| TCA | TTA | GAT | AAT | CTA | CAA | TCA | AGT | GAT | TTT | GGT | TAT | TTT | GAA | AGT | GCC | 1728 |
| Ser | Leu | Asp | Asn | Leu | Gln | Ser | Ser | Asp | Phe | Gly | Tyr | Phe | Glu | Ser | Ala | |
| | | | | 565 | | | | | 570 | | | | | 575 | | |
| AAT | GCT | TTT | ACA | TCT | TCA | TTA | GGT | AAT | ATA | GTA | GGT | GTT | AGA | AAT | TTT | 1776 |
| Asn | Ala | Phe | Thr | Ser | Ser | Leu | Gly | Asn | Ile | Val | Gly | Val | Arg | Asn | Phe | |
| | | | 580 | | | | | 585 | | | | | 590 | | | |
| AGT | GGG | ACT | GCA | GGA | GTG | ATA | ATA | GAC | AGA | TTT | GAA | TTT | ATT | CCA | GTT | 1824 |
| Ser | Gly | Thr | Ala | Gly | Val | Ile | Ile | Asp | Arg | Phe | Glu | Phe | Ile | Pro | Val | |
| | | 595 | | | | | 600 | | | | | 605 | | | | |
| ACT | GCA | ACA | CTC | GAG | GCT | GAA | TAT | AAT | CTG | GAA | AGA | GCG | CAG | AAG | GCG | 1872 |

|  |  |  |  |  |  |  |  |  |  |  |  |  |  |  |  |
|---|---|---|---|---|---|---|---|---|---|---|---|---|---|---|---|
| Thr | Ala | Thr | Leu | Glu | Ala | Glu | Tyr | Asn | Leu | Glu | Arg | Ala | Gln | Lys | Ala |
|  | 610 |  |  |  | 615 |  |  |  |  | 620 |  |  |  |  |  |

```
GTG  AAT  GCG  CTG  TTT  ACG  TCT  ACA  AAC  CAA  CTA  GGG  CTA  AAA  ACA  AAT         1920
Val  Asn  Ala  Leu  Phe  Thr  Ser  Thr  Asn  Gln  Leu  Gly  Leu  Lys  Thr  Asn
625                      630                     635                          640

GTA  ACG  GAT  TAT  CAT  ATT  GAT  CAA  GTG  TCC  AAT  TTA  GTT  ACG  TAT  TTA         1968
Val  Thr  Asp  Tyr  His  Ile  Asp  Gln  Val  Ser  Asn  Leu  Val  Thr  Tyr  Leu
                    645                     650                          655

TCG  GAT  GAA  TTT  TGT  CTG  GAT  GAA  AAG  CGA  GAA  TTG  TCC  GAG  AAA  GTC         2016
Ser  Asp  Glu  Phe  Cys  Leu  Asp  Glu  Lys  Arg  Glu  Leu  Ser  Glu  Lys  Val
               660                     665                     670

AAA  CAT  GCG  AAG  CGA  CTC  AGT  GAT  GAA  CGC  AAT  TTA  CTC  CAA  GAT  TCA         2064
Lys  His  Ala  Lys  Arg  Leu  Ser  Asp  Glu  Arg  Asn  Leu  Leu  Gln  Asp  Ser
          675                     680                     685

AAT  TTC  AAA  GAC  ATT  AAT  AGG  CAA  CCA  GAA  CGT  GGG  TGG  GGC  GGA  AGT         2112
Asn  Phe  Lys  Asp  Ile  Asn  Arg  Gln  Pro  Glu  Arg  Gly  Trp  Gly  Gly  Ser
     690                     695                     700

ACA  GGG  ATT  ACC  ATC  CAA  GGA  GGG  GAT  GAC  GTA  TTT  AAA  GAA  AAT  TAC         2160
Thr  Gly  Ile  Thr  Ile  Gln  Gly  Gly  Asp  Asp  Val  Phe  Lys  Glu  Asn  Tyr
705                     710                     715                     720

GTC  ACA  CTA  TCA  GGT  ACC  TTT  GAT  GAG  TGC  TAT  CCA  ACA  TAT  TTG  TAT         2208
Val  Thr  Leu  Ser  Gly  Thr  Phe  Asp  Glu  Cys  Tyr  Pro  Thr  Tyr  Leu  Tyr
                    725                     730                     735

CAA  AAA  ATC  GAT  GAA  TCA  AAA  TTA  AAA  GCC  TTT  ACC  CGT  TAT  CAA  TTA         2256
Gln  Lys  Ile  Asp  Glu  Ser  Lys  Leu  Lys  Ala  Phe  Thr  Arg  Tyr  Gln  Leu
               740                     745                     750

AGA  GGG  TAT  ATC  GAA  GAT  AGT  CAA  GAC  TTA  GAA  ATC  TAT  TTA  ATT  CGC         2304
Arg  Gly  Tyr  Ile  Glu  Asp  Ser  Gln  Asp  Leu  Glu  Ile  Tyr  Leu  Ile  Arg
          755                     760                     765

TAC  AAT  GCA  AAA  CAT  GAA  ACA  GTA  AAT  GTG  CCA  GGT  ACG  GGT  TCC  TTA         2352
Tyr  Asn  Ala  Lys  His  Glu  Thr  Val  Asn  Val  Pro  Gly  Thr  Gly  Ser  Leu
     770                     775                     780

TGG  CCG  CTT  TCA  GCC  CAA  AGT  CCA  ATC  GGA  AAG  TGT  GGA  GAG  CCG  AAT         2400
Trp  Pro  Leu  Ser  Ala  Gln  Ser  Pro  Ile  Gly  Lys  Cys  Gly  Glu  Pro  Asn
785                     790                     795                     800

CGA  TGC  GCG  CCA  CAC  CTT  GAA  TGG  AAT  CCT  GAC  TTA  GAT  TGT  TCG  TGT         2448
Arg  Cys  Ala  Pro  His  Leu  Glu  Trp  Asn  Pro  Asp  Leu  Asp  Cys  Ser  Cys
                    805                     810                     815

AGG  GAT  GGA  GAA  AAG  TGT  GCC  CAT  CAT  TCG  CAT  CAT  TTC  TCC  TTA  GAC         2496
Arg  Asp  Gly  Glu  Lys  Cys  Ala  His  His  Ser  His  His  Phe  Ser  Leu  Asp
               820                     825                     830

ATT  GAT  GTA  GGA  TGT  ACA  GAC  TTA  AAT  GAG  GAC  CTA  GGT  GTA  TGG  GTG         2544
Ile  Asp  Val  Gly  Cys  Thr  Asp  Leu  Asn  Glu  Asp  Leu  Gly  Val  Trp  Val
          835                     840                     845

ATC  TTT  AAG  ATT  AAG  ACG  CAA  GAT  GGG  CAC  GCA  AGA  CTA  GGG  AAT  CTA         2592
Ile  Phe  Lys  Ile  Lys  Thr  Gln  Asp  Gly  His  Ala  Arg  Leu  Gly  Asn  Leu
     850                     855                     860

GAG  TTT  CTC  GAA  GAG  AAA  CCA  TTA  GTA  GGA  GAA  GCG  CTA  GCT  CGT  GTG         2640
Glu  Phe  Leu  Glu  Glu  Lys  Pro  Leu  Val  Gly  Glu  Ala  Leu  Ala  Arg  Val
865                     870                     875                     880

AAA  AGA  GCG  GAG  AAA  AAA  TGG  AGA  GAC  AAA  CGT  GAA  AAA  TTG  GAA  TGG         2688
Lys  Arg  Ala  Glu  Lys  Lys  Trp  Arg  Asp  Lys  Arg  Glu  Lys  Leu  Glu  Trp
                    885                     890                     895

GAA  ACA  AAT  ATC  GTT  TAT  AAA  GAG  GCA  AAA  GAA  TCT  GTA  GAT  GCT  TTA         2736
Glu  Thr  Asn  Ile  Val  Tyr  Lys  Glu  Ala  Lys  Glu  Ser  Val  Asp  Ala  Leu
               900                     905                     910

TTT  GTA  AAC  TCT  CAA  TAT  GAT  CAA  TTA  CAA  GCG  GAT  ACG  AAT  ATT  GCC         2784
Phe  Val  Asn  Ser  Gln  Tyr  Asp  Gln  Leu  Gln  Ala  Asp  Thr  Asn  Ile  Ala
          915                     920                     925

ATG  ATT  CAT  GCG  GCA  GAT  AAA  CGT  GTT  CAT  AGC  ATT  CGA  GAA  GCT  TAT         2832
```

| | | | | | | | | | | | | | | |
|---|---|---|---|---|---|---|---|---|---|---|---|---|---|---|
| Met | Ile | His | Ala | Ala | Asp | Lys | Arg | Val | His | Ser | Ile | Arg | Glu | Ala | Tyr |
| | 930 | | | | | 935 | | | | | 940 | | | | |

| CTG | CCT | GAG | CTG | TCT | GTG | ATT | CCG | GGT | GTC | AAT | GCG | GCT | ATT | TTT | GAA | 2880 |
|---|---|---|---|---|---|---|---|---|---|---|---|---|---|---|---|---|
| Leu | Pro | Glu | Leu | Ser | Val | Ile | Pro | Gly | Val | Asn | Ala | Ala | Ile | Phe | Glu | |
| 945 | | | | | 950 | | | | | 955 | | | | | 960 | |

| GAA | TTA | GAA | GGG | CGT | ATT | TTC | ACT | GCA | TTC | TCC | CTA | TAT | GAT | GCG | AGA | 2928 |
|---|---|---|---|---|---|---|---|---|---|---|---|---|---|---|---|---|
| Glu | Leu | Glu | Gly | Arg | Ile | Phe | Thr | Ala | Phe | Ser | Leu | Tyr | Asp | Ala | Arg | |
| | | | | 965 | | | | | 970 | | | | | 975 | | |

| AAT | GTC | ATT | AAA | AAT | GGT | GAT | TTT | AAT | AAT | GGC | TTA | TCC | TGC | TGG | AAC | 2976 |
|---|---|---|---|---|---|---|---|---|---|---|---|---|---|---|---|---|
| Asn | Val | Ile | Lys | Asn | Gly | Asp | Phe | Asn | Asn | Gly | Leu | Ser | Cys | Trp | Asn | |
| | | | 980 | | | | | 985 | | | | | 990 | | | |

| GTG | AAA | GGG | CAT | GTA | GAT | GTA | GAA | GAA | CAA | AAC | AAC | CAA | CGT | TCG | GTC | 3024 |
|---|---|---|---|---|---|---|---|---|---|---|---|---|---|---|---|---|
| Val | Lys | Gly | His | Val | Asp | Val | Glu | Glu | Gln | Asn | Asn | Gln | Arg | Ser | Val | |
| | | 995 | | | | | 1000 | | | | | 1005 | | | | |

| CTT | GTT | GTT | CCG | GAA | TGG | GAA | GCA | GAA | GTG | TCA | CAA | GAA | GTT | CGT | GTC | 3072 |
|---|---|---|---|---|---|---|---|---|---|---|---|---|---|---|---|---|
| Leu | Val | Val | Pro | Glu | Trp | Glu | Ala | Glu | Val | Ser | Gln | Glu | Val | Arg | Val | |
| | 1010 | | | | | 1015 | | | | | 1020 | | | | | |

| TGT | CCG | GGT | CGT | GGC | TAT | ATC | CTT | CGT | GTC | ACA | GCG | TAC | AAG | GAG | GGA | 3120 |
|---|---|---|---|---|---|---|---|---|---|---|---|---|---|---|---|---|
| Cys | Pro | Gly | Arg | Gly | Tyr | Ile | Leu | Arg | Val | Thr | Ala | Tyr | Lys | Glu | Gly | |
| 1025 | | | | | 1030 | | | | | 1035 | | | | | 1040 | |

| TAT | GGA | GAA | GGT | TGC | GTA | ACC | ATT | CAT | GAG | ATC | GAG | AAC | AAT | ACA | GAC | 3168 |
|---|---|---|---|---|---|---|---|---|---|---|---|---|---|---|---|---|
| Tyr | Gly | Glu | Gly | Cys | Val | Thr | Ile | His | Glu | Ile | Glu | Asn | Asn | Thr | Asp | |
| | | | | 1045 | | | | | 1050 | | | | | 1055 | | |

| GAA | CTG | AAG | TTT | AGC | AAC | TGC | GTA | GAA | GAG | GAA | ATC | TAT | CCA | AAT | AAC | 3216 |
|---|---|---|---|---|---|---|---|---|---|---|---|---|---|---|---|---|
| Glu | Leu | Lys | Phe | Ser | Asn | Cys | Val | Glu | Glu | Glu | Ile | Tyr | Pro | Asn | Asn | |
| | | | 1060 | | | | | 1065 | | | | | 1070 | | | |

| ACG | GTA | ACG | TGT | AAT | GAT | TAT | ACT | GTA | AAT | CAA | GAA | GAA | TAC | GGA | GGT | 3264 |
|---|---|---|---|---|---|---|---|---|---|---|---|---|---|---|---|---|
| Thr | Val | Thr | Cys | Asn | Asp | Tyr | Thr | Val | Asn | Gln | Glu | Glu | Tyr | Gly | Gly | |
| | | 1075 | | | | | 1080 | | | | | 1085 | | | | |

| GCG | TAC | ACT | TCT | CGT | AAT | CGA | GGA | TAT | AAC | GAA | GCT | CCT | TCC | GTA | CCA | 3312 |
|---|---|---|---|---|---|---|---|---|---|---|---|---|---|---|---|---|
| Ala | Tyr | Thr | Ser | Arg | Asn | Arg | Gly | Tyr | Asn | Glu | Ala | Pro | Ser | Val | Pro | |
| | 1090 | | | | | 1095 | | | | | 1100 | | | | | |

| GCT | GAT | TAT | GCG | TCA | GTC | TAT | GAA | GAA | AAA | TCG | TAT | ACA | GAT | GGA | CGA | 3360 |
|---|---|---|---|---|---|---|---|---|---|---|---|---|---|---|---|---|
| Ala | Asp | Tyr | Ala | Ser | Val | Tyr | Glu | Glu | Lys | Ser | Tyr | Thr | Asp | Gly | Arg | |
| 1105 | | | | | 1110 | | | | | 1115 | | | | | 1120 | |

| AGA | GAG | AAT | CCT | TGT | GAA | TTT | AAC | AGA | GGG | TAT | AGG | GAT | TAC | ACG | CCA | 3408 |
|---|---|---|---|---|---|---|---|---|---|---|---|---|---|---|---|---|
| Arg | Glu | Asn | Pro | Cys | Glu | Phe | Asn | Arg | Gly | Tyr | Arg | Asp | Tyr | Thr | Pro | |
| | | | | 1125 | | | | | 1130 | | | | | 1135 | | |

| CTA | CCA | GTT | GGT | TAT | GTG | ACA | AAA | GAA | TTA | GAA | TAC | TTC | CCA | GAA | ACC | 3456 |
|---|---|---|---|---|---|---|---|---|---|---|---|---|---|---|---|---|
| Leu | Pro | Val | Gly | Tyr | Val | Thr | Lys | Glu | Leu | Glu | Tyr | Phe | Pro | Glu | Thr | |
| | | | 1140 | | | | | 1145 | | | | | 1150 | | | |

| GAT | AAG | GTA | TGG | ATT | GAG | ATT | GGA | GAA | ACG | GAA | GGA | ACA | TTT | ATC | GTG | 3504 |
|---|---|---|---|---|---|---|---|---|---|---|---|---|---|---|---|---|
| Asp | Lys | Val | Trp | Ile | Glu | Ile | Gly | Glu | Thr | Glu | Gly | Thr | Phe | Ile | Val | |
| | | | 1155 | | | | | 1160 | | | | | 1165 | | | |

| GAC | AGC | GTG | GAA | TTA | CTC | CTT | ATG | GAG | GAA | TAG | | | | | | 3537 |
|---|---|---|---|---|---|---|---|---|---|---|---|---|---|---|---|---|
| Asp | Ser | Val | Glu | Leu | Leu | Leu | Met | Glu | Glu | | | | | | | |
| | 1170 | | | | | 1175 | | | | | | | | | | |

CONTROL OF OSTRINIA

This application is a divisional of application Ser. No. 08/377,690, filed Jan. 25, 1995, which is a continuation of application Ser. No. 08/164,781, filed Dec. 10, 1993, now abandoned, which is a continuation of application Ser. No. 07/938,362, filed Aug. 31, 1992, now abandoned.

This invention relates to a method to control or combat Ostrinia, particularly *Ostrinia nubilalis* (Lepidoptera, Pyralidae) or the European corn borer, using a *Bacillus thuringiensis* ("Bt") cryIB gene or CryIB protein or using the cryIB gene and the cryIAb or cryIAc gene or their respective proteins. This invention also relates to a method to protect crops, particularly corn, against Ostrinia.

This invention further relates to the use of microorganisms, especially plant-associated microorganisms, preferably *Clavibacter xyli*, and to the use of plants, especially monocotyledonous plants, particularly corn (maize, Zea mays), stably transformed with the cryIB gene alone or with both the cryIB gene and cryIAb or cryIAc gene to control or combat Ostrinia such as *O. nubilalis*.

This invention still further relates to the use of insecticidal formulations containing the CryIB protein or both the CryIB protein and the CryIAb or CryIAc protein to protect plants from Ostrinia.

This invention also relates to a plant, especially a monocot, particularly a cereal plant, quite particularly corn, infestable by *O. nubilalis* and transformed with an expressible cryIB gene or with both an expressible cryIB gene and a cryIAb or cryIAc gene, to combat or control Ostrinia.

BACKGROUND OF THE INVENTION

*Bacillus thuringiensis*

*Bacillus thuringiensis* ("Bt") is a gram-positive soil bacterium, which produces endogenous crystalline inclusions upon sporulation. Early in this century, these bacteria were found to be insecticidal (Berliner, 1915). Some years later, their insecticidal activity was found to reside in the proteins present in their crystals, hereinafter referred to as "insecticidal crystal proteins" or "ICPs". Since then, the Bt strains, spores, crystals and ICPs have been used as biological insecticides in commercial formulations.

The limited spectrum of these insecticidal proteins allows any naturally occurring predators of the target insects to survive. The continued presence of these predators prevents further outbreaks of the insects. Furthermore, these Bt proteins have the advantage that they are rapidly degradable and that no stable residues accumulate in the environment.

Cry proteins and cry genes

The specificity of the environmentally safe Bt insecticides has provoked a search for new Bt strains, producing toxins against other insect pests. Insecticidal Bt strains toxic to lepidopteran, coleopteran and dipteran insects have been found (Höfte and Whiteley, 1989). Although considerable homology can be found between genes that encode various ICPs toxic to one particular insect class, the sensitivity of specific insects to related Bt gene products is often very different. For instance, Chambers et al (1991) described a large difference in activity of the CryIF protein against *Heliothis virescens* and *Heliothis zea* (50% lethal concentrations of respectively 0.31 and >57 ng protoxin/mm$^2$ diet).

The Bt insecticidal crystal (Cry) proteins have been divided into five classes, according to their structural similarities and insecticidal spectra (Höfte and Whiteley, 1989): CryI proteins are toxic to Lepidoptera, CryII proteins are toxic to Diptera and Lepidoptera, CryIII proteins are toxic to Coleoptera and CryIV proteins are toxic to Diptera. A general cytolytic protein (cytA) is classified as a fifth toxic protein, but it has no specific insecticidal activity. The Bt genes coding for the insecticidal Cry proteins (cry genes) show strong homology in some conserved domains. These insecticidal Bt genes are mostly found on large conjugative plasmids, which may explain their observed mobility among Bt strains. One strain can contain several cry genes, and one gene can be found in several strains (Höfte and Whiteley, 1989).

Typically, cryI genes encode proteins with a molecular weight of 130 to 140 kD (hereinafter referred to as the "protoxins"), and upon ingestion by a sensitive insect, the protoxins are processed to smaller proteins (hereinafter referred to as the "toxins") having a molecular weight of 60 to 70 kD. The cryII and cryIII genes encode protoxins with a molecular weight of about 70 kD (except the cryIIIC gene which encodes a protoxin of 129 kD according to PCT publication WO 90/09445). The CryIV genes encode protoxins of either of these molecular weight types. The CryI protoxins constitute the largest group of protoxins, which are found in typical bipyramidal crystals.

The cry genes have been used to transform bacteria (e.g., Obukowicz et al, 1986; Stock et al, 1990) and plants (e.g., Vaeck et al, 1987) in order to provide resistance against insect pests. Adequate expression in plants was only obtained when the plants were transformed with a truncated Bt gene (e.g., Vaeck et al, 1987; Fischhoff et al, 1987; Barton et al, 1987).

The cryIB gene has been described in European patent publication ("EP") 408 403 and by Brizzard and Whiteley (1988). It encodes a 137 kD protoxin and a 66 kD toxin. The CryIB toxin has been shown to be insecticidal to insects like *Pieris brassicae, Plutella xylostella, Spadoptera littoralis* and *Spodoptera exigua* (Ferré et al, 1991; Visser et al, The CryIAa (Gawron-Burke and Baum, 1991), CryIAb, CryIAc (Macintosh et al, 1990) and CryIF gene products (Chambers et al, 1991) have been described as toxic to *O. nubilalis*. Moreover, Peferoen (1991) has described the insecticidal activity of the following ICPs against various insects, including *O. nubilalis*: CryIAa, CryIAb, CryIAc, CryIB, CryID, CryIC and CryIE, and PCT publication WO 92/09696 also has described the insecticidal activity of the cryIAb and cryIB genes against *O. nubilalis*.

PCT publication 90/15139 has described the prevention of insect resistance development with various combinations of Bt genes, such as the cryIAb and cryIB genes (the Bt 2 and Bt 14 genes), against *Pieris brassicae, Plutella xylostella*, and *Phthorimaea operculella*.

Mode of action of the CryI proteins

The ICPs owe their specificity to the presence of specific receptor sites in the midgut brush border membranes of sensitive insects. In vivo, the crystals are solubilized in the alkaline environment of the midgut, and the released protoxins are processed by proteases to yield smaller protease-resistant toxins which bind to, and cause swelling of, the midgut cells (Gill et al, 1992). The C-terminal part of the CryI-type protoxin is probably involved in the formation of its crystal structure, but is thought not to be important in its mode of action (Höfte and Whiteley, 1989). Electrophysiological evidence (Harvey et al, 1983) and biochemical evidence (Knowles and Ellar, 1987) suggest that the toxins generate pores in the midgut brush border cell membranes, thus disturbing the osmotic balance. The intoxicated insects quickly stop feeding and eventually die. The high affinity binding of the toxins has been correlated with their toxicity (Van Rie et al, 1989).

*Ostrinia nubilalis*

The European corn borer is a very serious and persistant pest for corn (Davidson and Lyon, 1987; Hudon et al, 1987). The larvae of this insect initially feed on leaf tissue and later enter the stalks, burrowing downwards as the season progresses. *O. nubilalis* is estimated to be the most important corn pest in Europe and the second most important in the USA. Damage caused by *O. nubilalis* in the USA is estimated to be over 400 million dollars (U.S.) a year. Estimates for *O. nubilalis* spraying amount in France to 25 million dollars (U.S.) a year. Up to now, hazardous chemical insecticides have mostly been used to combat this insect. The European corn borer is remarkably polyphagous (Hudon et al, 1987) and has been found to attack other important crops such as wheat, cotton, potato, tomato, beet, oat and soybean plants (Davidson and Lyon, 1987; Hudon et al, 1987).

SUMMARY OF THE INVENTION

In accordance with this invention, a method is provided to combat and/or control insects of the species Ostrinia, particularly *Ostrinia nubilalis* (the European corn borer), by the step of contacting these insects with: a) the CryIB protein or an equivalent thereof; or b) both i) the CryIB protein and ii) the CryIAb or the CryIAc, preferably the CryIAb, protein or their equivalents.

Also in accordance with this invention, the contacting step can be carried out with an insecticidal composition comprising: the CryIB protein or its equivalent or both the CryIB protein and the CryIAb or CryIAc protein or their equivalents in pure form; or Bt crystals containing these protein(s) or their equivalents; or crystal-spore mixtures of naturally occurring Bt bacteria containing the cryIB gene or its equivalent or both the cryIB gene and the cryIAb or cryIAc gene or their equivalents; or crystal-spore mixtures of Bt bacteria transformed with an expressible cryIB gene or its equivalent or with both an expressible cryIB gene and an expressible cryIAb or cryIAc gene or their equivalents.

Further in accordance with this invention, the contacting step can be carried out with a microorganism, preferably a plant-associated microorganism, especially an endophytic microorganism, particularly *Clavibacter xyli*, transformed with an expressible cryIB gene or its equivalent or with both an expressible cryIB gene and an expressible cryIAb or cryIAc gene or their equivalents, so as to inoculate plants or parts thereof, such as seeds, so that they become resistant to attack by Ostrinia.

Furthermore, the contacting of the insects can be with a plant, especially a monocotyledonous plant, particularly a cereal plant, quite particularly corn, stably transformed with an expressible cryIB gene or its equivalent or with both an expressible cryIAb or cryIAc gene and an expressible cryIB gone or their equivalents, so that the transformed plant expresses the CryIB protein or its equivalent or a combination of the CryIB and CryIAb or CryIAc proteins or their equivalents in insecticidally effective amounts.

Moreover, a plant, especially a monocotyledonous plant, particularly a cereal plant, quite particularly a corn plant, infested by Ostrinia, is protected from this insect by having been stably transformed with the cryIB gene or its equivalent or with both the cryIB gene and the cryIAb or cryIAc gene or their equivalents.

DETAILED DESCRIPTION OF THE INVENTION

This invention is based on the result of toxicity assays which were conducted by feeding the European corn borer, *Ostrinia nubilalis,* an artificial diet containing the purified CryIB toxin and which surprisingly showed that this protein was toxic to the European corn borer (see Example 1). Furthermore, the CryIB toxin was found to bind non-competitively to the midgut membranes of Ostrinia when compared with other Cry toxins which are insecticidally active against this insect as shown in Example 2. Therefore, this active Bt protein can be used to provide maximum protection against this important pest and can prevent or reduce the development of insect resistance to Bt insecticidal formulations in the field.

The "CryIB protein" of this invention encompasses the full length protein (protoxin) encoded by the cryIB gene and having the amino acid sequence shown in SEQ ID No.1 of the Sequence Listing and any protein that is substantially the same as the CryIB protoxin of SEQ ID No.1, as well as any insecticidally active fragment thereof, such as the CryIB toxin. An example of substantially the same protein as the protoxin of SEQ ID No.1 is the naturally occurring CryIB protoxin described by Brizzard and Whiteley (1988). The "CryIB protein" of this invention includes proteins in which some amino acids of the protoxin of SEQ ID No.1 are deleted, added or replaced by others without significantly changing the insecticidal activity, particularly against *O. nubilalis,* for example the modified CryIB protoxin described in EP 408 403 "CryIB toxin" as used herein, means the smallest insecticidally active fragment of the CryIB protoxin, extending from amino acid 145 to amino acid 636 in SEQ ID No.1. In this regard, "insecticidally active fragment of the CryIB protoxin" as used herein, means any part of the CryIB protoxin having insecticidal activity, preferably its toxin.

In this invention, "cryIB gene" encompasses the gene with the DNA sequence shown in SEQ ID No.1 of the Sequence Listing or any mutant, synthetic or modified gene encoding a CryIB protein, such as the modified gene described in EP 408 403. Modifications to the gene can include: 1) the replacement of some codons with others coding for the same or for other amino acids, preferably with codons that code for the same amino acids; 2) deleting or adding some codons; and 3) reciprocal recombination as described by Ge et al (1991); provided that such modifications do not substantially alter the properties, especially the insecticidal properties, particularly against *O. nubilalis,* of the encoded CryIB protein. It is evident that the definition of the cryIB gene comprises any modified gene designed to provide higher expression levels of a CryIB protein in plants. One particularly preferred modified gene is the naturally occurring cryIB gene described by Brizzard and Whiteley (1988), wherein only two nucleotides are different from SEQ ID No.1: in the Brizzard and Whiteley sequence, a T is replaced by a C at position 311, and a C is replaced by a T at position 633. Only the latter change in Brizzard and Whiteley leads to a different amino acid: a His codon is changed to a Tyr codon. "Insecticidally active fragment of the cryIB gene", as used herein, means any truncated gene encoding an insecticidally active fragment of the CryIB protein, like the gene fragment encoding the CryIB toxin.

In accordance with this invention, a cryIB gene can be isolated from a Bt strain, for example Bt. entomocidus HD-110. This strain is publicly available from the Agricultural Research Culture Collection, Northern Regional Research Laboratory, U.S. Dept. of Agriculture, Peoria, Ill. 61604, USA ("NRRL"). The isolation and cloning of the cryIB gene, as well as its modification, are described in EP 408 403. The gene has an open reading frame (ORF) of 3684 bp, encoding a 137 kD protoxin and 66 kD and 55 kD protease-activated fragments. The nucleotide sequence and the corresponding amino acid sequence are shown in SEQ ID No.1. An insecticidally active cryIB gene fragment also can be constructed as described in EP 408 403. For this purpose, a BcII site has been identified downstream of the coding sequence encoding the CryIB toxin.

Similarly, the "CryIAb protein" of this invention encompasses a protoxin with the amino acid sequence disclosed in EP 193 259 and shown in SEQ ID No.2 in the Sequence Listing, any protein that is substantially the same as the CryIAb protoxin of SEQ ID No.2, and any insecticidally active fragment thereof, such as the CryIAb toxin. The CryIAb protein includes: naturally occurring variants with substantially the same insecticidal activity, particularly against *O. nubilalis,* such as the CryIAb protoxin described by Höfte and Whiteley (1989) and in EP 224 331 and the CryIAb protoxin described by Fischhoff et al (1987); and any CryIAb protoxin encoded by a modified or synthetic Bt gene but with substantially the same insecticidal activity as the protoxin of SEQ ID No.2, as described, for example, in PCT publication WO 91/16432 and in European patent applications ("EPA") 91402920.2 and 92400820.4. "CryIAb toxin", as used herein, is the protein containing amino acids 29 to 601 of the amino acid sequence shown in SEQ ID No.2 in the Sequence Listing. "Insecticidally active fragment of the CryIAb protein", as used herein, means any fragment of the CryIAb protoxin having insecticidal activity, preferably the cryIAb toxin.

Similarly, the "cryIAb gene" of this invention encompasses the gene with the DNA sequence shown in SEQ ID No.2 or any mutant, synthetic or modified gene encoding a CryIAb protein. Naturally occurring cryIAb genes with minor differences include the gene described in EP 224 331 and the genes listed by Höfte and Whiteley (1989). Modifications, as described above for the cryIB gene, can also be introduced into the cryIAb gene, provided that such modifications do not substantially alter the insecticidal properties, particularly against *O. nubilalis,* of the encoded CryIAb protein. The isolation and cloning of a cryIAb gene is described in EP 193 259 and by Höfte et al (1986). The gene contains an ORF of 3464 bp, encoding a protoxin of 131 kD and a toxin of 60 kD. The gene can be isolated from the Bt subsp. *thuringiensis berliner* 1715 strain (Höfte et al, 1986) or from the Bt HD-1 kurstaki strain which is publicly available from the N.R.R.L.

Likewise, the "CryIAc protein" of this invention encompasses a protoxin with the amino acid sequence shown in SEQ ID No.3 of the Sequence Listing, any protein that is substantially the same as the CryIAc protoxin of SEQ ID No.3 and any insecticidally active fragment thereof, such as the CryIAc toxin described by Dardenne et al (1990).

Likewise, the "cryIAc gene" of this invention encompasses the gene described by Adang et al (1985) with the DNA sequence as shown in SEQ ID No.3 of the Sequence listing or any mutant, synthetic or modified gene, encoding a CryIAc protein. Variants of the cryIAc gene include: the modified or synthetic cryIAc genes described in EP 358 962; and the naturally occurring cryIAc gene described by Dardenne et al (1990), EP 367 474, and PCT publication WO 90/03434 which is a preferred variant differing from the cryIAc DNA sequence of SEQ ID No.3 by 10 nucleotides in the gene part-encoding the toxin (one nucleotide triplet also being deleted in this part, resulting in 3 different amino acids in the toxin and one deleted amino acid). The cryIAc gene can be isolated from the Bt subsp. thuringiensis HD-73 strain, publicly available from the NRRL.

In accordance with this invention, one can combat or control Ostrinia species, particularly the European corn borer, by contacting this insect: a) with the CryIB protein or b) with a combination of the CryIB protein and the CryIAb protein or a combination of the CryIB protein and the CryIAc protein, preferably the combination of the CryIB and CryIAb proteins. Such combinations of proteins encompass combinations of the full length protoxins and/or insecticidally active fragments .of such protoxins, achieved for example by co-expression of the corresponding genes and gene fragments in a cell or by expression of a modified gene encoding insecticidally active fragments of both proteins. By "combat" is meant treating plants in a field in such a way as to destroy the Ostrinia (e.g. European corn borers) that are attacking or that would attack the plants such as when a sudden increase in its population would occur; by "control" is meant treating plants in a field in such a way as to limit the Ostrinia's damage to the plants such as when relatively small numbers of insects are constantly present in the field without causing major damage to the plants; and by "contacting" is meant ensuring that the CryIB protein or a combination of the CryIB and CryIAb or CryIAc proteins is present in a field of plants that is infested, or can be infested, by Ostrinia so that the protein(s) can become ingested by the insects, for example by transforming either the plants, plant-associated microorganisms or other microorganisms, or by applying to the field insecticidal formulations containing the CryIB protein or the combination of the CryIB protein and the CryIAb or CryIAc protein.

Contacting Ostrinia with the CryIB protein or a mixture thereof with the CryIAb or CryIAc protein in accordance with this invention can be carried out directly by using an insecticidal composition comprising the CryIB protein or both the CryIB and CryIAb or CryIAc proteins in the form of purified proteins, in the form of Bt strains or their crystals, or in the form of Bt crystal-spore mixtures. By "purified proteins" is meant the CryIB, CryIAb and/or CryIAc proteins purified from their crystal proteins, from transformed microorganisms or from transformed plant cells by methods well known in the art (e.g., as described in EP 193 259). In this regard, such a contacting step can be carried out with naturally occurring or genetically engineered Bt strains, preferably the Bt subsp. entomocidus HD-110, Bt subsp. thuringiensis HD-2 or Bt subsp. thuringiensis 4412 strain (Höfte et al, 1986; Höfte and Whiteley, 1989), containing the cryIB gene or both the cryIB and cryIAb genes. For contacting the insects with both the CryIB and CryIAb protoxins, the Bt subsp. thuringiensis HD-2 strain is preferred, since it has been found to comprise both the cryIB and cryIAb genes (Brizzard et al, 1991).

An insecticidal, particularly an anti-Ostrinia, composition comprising the CryIB protein or the CryIB and the CryIAb or CryIAc proteins can be formulated in a conventional manner, together with suitable carriers, diluents, emulsifiers and/or dispersants known in the art. Also, well known methods for stabilizing Cry proteins in the field can be used, such as by delivering the proteins to the field in killed and stabilized microorganisms, or targeting the proteins, synthesized by plants or microorganisms transformed with the cryIB gene or the cryIAb or cryIAc and the cryIB genes to certain intra- or extracellular sites where a higher stability Of the proteins can be obtained.

The CryIB protein or the CryIB and CryIAb or CryIAc proteins or killed and stabilized cells of microorganisms containing such proteins can be formulated in insecticidal compositions in a variety of ways, using any number of conventional additives, wet or dry, depending upon the particular use. Additives can include wetting agents, detergents, stabilizers, adhering agents, spreading agents and extenders. Examples of such compositions include pastes, dusting powders, wettable powders, granules, baits and aerosol sprays. Other Bt proteins or killed and stabilized cells of microorganisms containing such proteins and other insecticides, as well as fungicides, biocides, herbicides and fertilizers, can be employed along with the CryIB protein or the CryIB and the CryIAb or CryIAc proteins or killed and stabilized cells containing such proteins to provide additional advantages or benefits. Such an insecticidal composition can be prepared in a conventional manner, and the amount of the CryIB protein or the CryIB and the CryIAb or CryIac proteins employed will depend upon a variety of factors, such as the composition used, the type of area to which the composition is to be applied, and the prevailing weather conditions, but generally the concentration of such proteins will be at least about 0.1% by weight of the formulation, more often from about 0.15% to about 0.8% by weight percent of the formulation.

The cryIB gene or the cryIB and the cryIAb or cryIAc genes can, if desired, also be used with their native 5' and 3' signal sequences, to transform microorganisms such as Bt strains, in order to control Ostrinia, particularly *O. nubilalis*. Of course, other microorganisms can be transformed, such as phages and other viruses, bacteria, fungi and yeasts. Such transformations can be carried out in a conventional manner, preferably by using conventional electroporation methods as described in PCT publication WO 90/06999 or other methods as described by Lereclus et al (1992). To obtain expression in microorganisms other than Bt, such cry genes will have to contain the necessary signal sequences to provide proper expression in such other microorganisms. The BtPGSI387 strain (PCT publication WO 90/06999) is particularly suited for transformation with such cry genes, since this strain is easily fermented by conventional methods (Dulmage, 1981) to provide high yields of cells. The so-transformed microorganism can then be used to produce the CryIB protein or the CryIB and the CryIAb or CryIAc proteins, which could then be formulated for protecting plants from Ostrinia.

Contacting Ostrinia, particularly the European corn borer, with the CryIB protein or mixtures thereof in accordance with this invention can also be carried out indirectly, by ensuring that the CryIB protein or the CryIB and the CryIAb or CryIAc proteins are biologically produced at appropriate places by microorganisms or plants expressing the cryIB gene or the cryIAb or cryIAc and the cryIB genes. This can be achieved by inoculating plants or parts of plants, like seeds, with plant-associated microorganisms, transformed with the cryIB gene or the cryIB and the cryIAb or cryIAc genes. By "inoculating" is meant contacting or coating a plant or part of a plant with the microorganisms such that they remain associated with the plant or plant parts. Plant-associated microorganisms, which can be used, include the plant-colonizing (epiphytic) microorganisms like the Pseudomonas bacteria and endophytic plant-colonizing microorganisms like *Clavibacter xyli*. Transformation of *Clavibacter xyli* subsp. cynodontis with the cryIB gene or the cryIB and the cryIAb or cryIAc genes can be carried out as described by Turner et al (1991), and these genes are preferably under the control of their original Bt promoter or any other Bt promoter and are flanked by suitable 3' transcription termination signals like the lambda $t_R1$ transcription terminator sequence (Turner et al, 1991). Stably transforming plants with the cryIB gene or with a combination of the cryIAb or cryIAc and the cryIB genes in accordance with this invention also renders the plants and their progeny resistant to Ostrinia.

In order to express the cryIB gene or the cryIB and the cryIAb or cryIAc genes in microorganisms and plants, suitable restriction sites can be introduced, flanking the gene(s). This can be done by site-directed mutagenesis (Stanssens et al, 1989).

In order to obtain enhanced expression in plants, it may be preferred to modify the cryIB, cryIAb and/or cryIAc genes as described: in PCT publication WO 91/16432, EPA 91402920.2 and 92400820.4 and by Perlak et al (1991) and Murray et al (1991). A particularly preferred modification to the cryIB gene involves changing the exceptional TTG start codon to the more common ATG start codon by site-directed mutagenesis (Stanssens et al, 1989) as described in EP 408 403.

A gene cassette, containing the cryIB gene or the cryIB and the cryIAb or cryIAc genes, can be constructed as described in EP 408 403 in order to express the gene(s) in *E. coli* and plants. In this regard, insecticidally effective part(s) of such gene(s) can be stably inserted in a conventional manner into the nuclear genome of a single plant cell, and the so-transformed plant cell can be used in a conventional manner to produce a stably transformed plant that is resistant to the European corn borer. In this regard, a disarmed Ti-plasmid, containing the insecticidally effective gene part(s), in *Agrobacterium tumefaciens* can be used to transform the plant cell using the procedures described, for example, in EP 116 718, EP 270 822, PCT publication WO 84/02913, Deblaere et al (1985), and Gould et al (1991). Preferred Ti-plasmid vectors contain the insecticidally effective gene part(s) between the border sequences, or at least located to the left of the right border sequence, of the T-DNA of the Ti-plasmid. Of course, other types of vectors can be used to transform the plant cell, such as direct gene transfer (as in EP 233 247), pollen-mediated transformation (as in PCT publication WO 85/01856), plant RNA virus-mediated transformation (as in EP 067 553), or liposome-mediated transformation (as in US patent 4,536,475). Other methods described for transforming certain lines of corn (Fromm et al, 1990; Gordon-Kamm et al, 1990) and the more recently described method for transforming monocots generally (PCT publication WO 92/09696) also can be used.

The resulting transformed plant can be used in a conventional plant breeding scheme to produce more transformed plants with the same characteristics or to introduce the insecticidally effective gene part(s) in other varieties of the same or related plant species. The seeds, obtained from these plants, contain the respective gene part(s) as stable genomic inserts. Cells of the transformed plant can be cultured to produce the gene products for use in conventional insecticidal compositions.

Part(s) of the cryIB or the cryIB and the cryIAb or cryIAc gene(s), encoding insecticidally active fragment(s) of the CryIB or the CryIB and the CryIAb or CryIAC proteins, are inserted in a plant cell genome so that the inserted gene part(s) are downstream (e.g. 3') of, and under the control of, a promoter which can direct the expression of the gene part(s) in the plant cell; and upstream (e.g. 5') of suitable 3' end transcription regulation signals (i.e., transcript formation and polyadenylation signals). Preferred promoters include: the strong constitutive 35S promoters of the cauliflower mosaic virus of isolates CM 1841 (Gardner et al, 1981), CabbB-S (Franck et al, 1980) and CabbB-JI (Hull and Howell, 1987); and the TR1' promoter and the TR2' promoter which drive the expression of the 1' and 2' genes, respectively, of the T-DNA (Velten et al, 1984). Alternative promoters are those which are selectively expressed in certain tissues or are inducible promoters (such as the promoter of the ribulose-1,5-bisphosphate carboxylase small subunit gene disclosed in EP 193 259). Preferred polyadenylation and transcript formation signals include those of the octopine synthase gene (Gielen et al, 1984) and the T-DNA gene 7 (Velten and Schell, 1985), which act as 3' untranslated DNA sequences in transformed plant cells. For example, the cryIB gene or the cryIB and the cryIAb or cryIAc genes can be inserted into the pDE110 or pDE108 vector, described in PCT patent publication WO 92/09696, under the control of suitable plant .promoters and flanked by suitable 3' termination sites as described above. These vectors can be used to stably transform corn lines with these genes (e.g., as described in PCT publication WO 92/09696), thus rendering the corn lines resistant to attack by Ostrinia, such as the European corn borer.

To achieve co-expression of the cryIB and the cryIAb or cryIAc gene(s) in plants, it is preferred that two plants, each transformed with one of the cry genes, be crossed to obtain a progeny, containing both genes as described, for example, in EP 408 403. The resulting plants are well protected against Ostrinia nubilalis attack by the expression of both the CryIB and the CryIAb or CryIAc proteins in the plant cells. Gene cassettes for co-expression of the cryIB and cryIAb genes in plants are described in EP 408 403. For obtaining enhanced expression in monocots such as corn, the cryIAb or cryIAc and the cryIB genes are preferably modified as described in PCT publication WO 91/16432 and in EPA 91402920.2 and 92400820.4. These modified genes can be transferred to a monocot cell by electroporation as disclosed in PCT publication WO 92/09696 to achieve expression of the genes in monocots after regeneration of the monocot cell to a plant.

It is also preferred to provide the transformed plant cells with screenable or selectable marker genes. Suitable marker genes include the neogene (Reiss et al, 1984; EP 242 236), coding for kanamycin resistance. The transformed cells can be provided with a hybrid gene, containing the cry gene(s) and the marker gene under the control of the same promoter. This hybrid gene will be expressed in the transformed cells as a fusion protein (Vaeck et al, 1987). Also hybrid genes, comprising the active fragments of both the cryIB and the cryIAb .or cryIAc genes, can be constructed as described by, for example, Ge et al (1991).

The following Examples illustrate the invention. In the Examples, all procedures for making and manipulating DNA are carried out by the standard procedures described by Sambrook et al (1989) *Molecular Cloning—A Laboratory Manual, Second Edition,* Cold Spring Harbor Laboratory Press, NY, USA.

In the Examples, references are made to the following Figures and Sequence Listing.

FIG. 1 shows the binding of iodinated CryIAb toxin to brush border membrane vesicles of *O. nubilalis*. Membrane vesicles were incubated (30 min.) with iodinated CryIAb toxin in the presence of increasing concentrations of competitor: unlabeled CryIAb (*), CryIAc (o) and CryIB (□) toxins. The CryIB toxins did not bind to the receptors occupied by the labeled CryIAb toxins, while the CryIAc and CryIAb toxins suppress binding of the LABELLED CryIAb toxins. Curves were predicted by the LIGAND computer program (Munson and Rodbard, 1980). Each point is the mean of three independent experiments (three independently prepared batches of vesicles).

SEQUENCE LISTING

SEQ ID No.1 is the nucleotide sequence of the cryIB gene and the corresponding amino acid sequence of the CryIB protoxin as described in EP 408 403.

SEQ ID No.2 is the nucleotide sequence of the cryIAb gene and the corresponding amino acid sequence of the CryIAb protoxin as described in EP 193 259.

SEQ ID No.3 is the nucleotide sequence of the cryIAc gene and the corresponding amino acid sequence of the CryIAc protoxin.

EXAMPLE 1

Insecticidal Activity of the CryIB Toxin

The CryIB toxin of SEQ ID No.1, obtained from *Bacillus thuringiensis* subsp. entomocidus HD-110, was found to be insecticidal to neonate *Ostrinia nubilalis* (European corn borer) larvae in bio-assays on artificial diet (diet according to Poitout et al, 1972).

Multiwell plates were filled with the artificial diet, and sample dilutions of different purified CryI toxins (50 μl) in bovine serum albumin-containing phosphate buffered saline ("PBS-BSA": 8 mM $Na_2HPO_4$, 2 mM $KH_2PO_4$, 150 mM NaCl and 0.1% BSA) were applied uniformly on the surface of the food and allowed to dry. Mortality was scored after 5 days. The toxicity data were analyzed by probit analysis (Finney, 1962).

As shown in Table I below, *O. nubilalis* is very sensitive to the CryIB toxin. The 50% lethal concentration value is much lower than most other CryI toxins and only the CryIAb toxin is more toxic. Also, the toxicity of the CryIB protoxin against *O. nubilalis* larvae was found to be comparable to that of the activated toxin, demonstrating that the proteolytical activation of the protoxin in the midgut did not interfere with toxicity.

TABLE I

| $LC_{50}$ values of solubilized purified CryI toxins to *O. nubilalis* ($LC_{50}$ expressed in ng toxin/$cm^2$ of diet). | | | | | | |
|---|---|---|---|---|---|---|
| CryI Toxin | IAa | IAb | IAc | IB | IC | ID | IE |
| $LC_{50}$ | 1247 | 50 | 531 | 105 | >1350 | >1350 | >1350 |

Upon spraying of corn plants with the CryIB toxin, the plants are protected from *O. nubilalis* larvae, which immediately stop feeding upon spraying and do not cause any major damage to the plants.

EXAMPLE 2

Binding of the CryIB, CryIAb and CryIAc toxins to *O. nubilalis* Midgut Membranes Receptor binding assays were conducted to compare the binding of the CryIB toxin with that of other CryI toxins. These tests were conducted on Ostrinia midgut brush border membrane vesicles, prepared as described by Wolfersberger et al (1987), using radioligand competition binding experiments as described by Van Rie et al (1989).

As shown in FIG. 1, the CryIAb and CryIAc toxins bind to the same receptor sites in the brush border membranes. However, no suppression of CryIAb binding is obtained when adding the CryIB toxin to the assay, indicating that the CryIB toxin binds to a different receptor.

Furthermore, immunocytochemical assays, using polyclonal antibodies against the CryIB toxin, showed accumulation of the toxin in the midgut and binding of the toxin to the brush border membranes in previously intoxicated European corn borer larvae.

These results show the surprising benefit of using the CryIB protein in combination with the CryIAb protein or the CryIAc protein, particularly with the CryIAb protein, against Ostrinia, particularly *O. nubilalis*.

4. REFERENCES

Adang, M. J.; Staver, M. J.; Rocheleau, T. A.; Leighton, J.; Barker, F. F. & Thompson, D. V. (1985). Gene 36, 289–300.

Barton, K. A.; Whiteley, H. R. & Yang, N.-S. (1987). Plant Physiology 85, 1103–1109.

Berliner, E. (1915). Zeitschr. Angew. Entomol. 2, 29.

Brizzard, B. L.; Schnepf, H. E. & Kronstad, J. W. (1991). Mol. Gen. Genet. 231, 59–64.

Brizzard, B. L. & Whiteley, H. R. (1988). Nucleic. Acids Res. 16, 4168–4169.

Chambers, J. A.; Jelen, A.; Pearce Gilbert, M.; Jany, C. S.; Johnson, T. B. & Gawron-Burke, C. (1991). J. Bacteriology 173, 3966–3976.

Dardenne, F.; Seurinck, J.; Lambert, B. and Perferoen, M. (1990). Nucl. Acids Res. 18, 5546.

Davidson, R. H. & Lyon, W. F. (1987). Insect pests of farm, garden and orchard, eds Davidson & Lyon. John Wiley and Sons, NY, eighth edition.

Deblaere, R.; Bytebier, B.; De Greve, H.; Deboeck, F.; Schell, J.; Van Montagu, M. & Leemans, J. (1985). Nucl. Acids Res. 13, 4777–4778.

Dulmage, H. T. (1981). Production of bacteria for biological control of insects. In Biological control in crop production, ed. Paparizas, D. C.; Osmun Publishers; Totowa, N.J., USA; pp. 129–141.

Ferré, J.; Real, M. D.; Van Rie, J.; Jansens, S. & Peferoen, M. (1991). Proc. Natl. Acad. Sci USA 88, 5119–5123.

Finney, D. (1962). Probit analysis. Cambridge University Press, Cambridge, pp. 50–80.

Fischhoff, D.A.; Bowdish, K. S.; Perlak, F. J.; Marrone, P. G.; McCormick, S. M.; Niedermeyer, J. G.; Dean, D. A.; Kusano-Kretzmer, K.; Mayer, E. J.; Rochester, D. E.; Rogers, S. G. & Fraley, R. T. (1987). Biotechnology 5, 807–813.

Franck, Guilley, Jonard, Richards & Hirth. (1980). Cell 21, 285–294.

Fromm, M. E.; Morrish, F.; Armstrong, C.; Williams, R.; Thomas, J. & Klein, T. M. (1990). Bio/Technology 8, 833–839.

Gardner, Howarth, Hahn, Brown-Luedi, Shepard & Messing. (1981). Nucl. Acids Res. 9, 2871–2887.

Gawron-Burke, C. & Baum, J. A. (1991). Gen. Eng. 13, 237–263.

Ge, A. Z.; Rivers, D.; Milne, R. & Dean, D. H. (1991). J. Biol. Chem. 266, 17954–17958.

Gielen, J.; De Beukeleer, M.; Seurinck, J.; Deboeck, F.; De Greve, H.; Lemmers, M.; Van Montagu, M. & Schell, J. (1984). EMBO J. 3, 835–845.

Gill, S. S.; Cowles, E. A. & Pietrantonio, P. V. (1992). Annu. Rev. Entomol. 37, 615–36.

Gordon-Kamm, W. J.; Spencer, T. M.; Mangano, M. L.; Adams, T. R.; Daines, R. J.; Start, W. G.; O'Brien, J. V.; Chambers, S. A.; Adams, W. R. Jr.; Willets, N. G.; Rice, T. B.; Mackey, C. J.; Krueger, R. W.; Kausch, A. P. & Lemaux, P. G. (1990). The Plant Cell 2, 603–618.

Gould, J.; Devey, M.; Hasegawa, O.; Ulian, E. C.; Peterson, G. & Smith, R. H. (1991). Plant Physiol. 95, 426–434.

Harvey, W. R.; Cioffi, M.; Dow, J. A. T. & Wolfersberger, M. G. (1983). J. Exp. Biol. 106, 91–117.

Höfte, H.; De Greve, H.; Seurinck, J.; Jansens, S.; Mahillon, J.; Ampe, C.; Vandekerckhove, J.; Vanderbruggen, H.; Van Montagu, M.; Zabeau, M. & Vaeck, M. (1986). Eur. J. Biochem. 161, 273–280.

Höfte, H. & Whiteley, H. R. (1989). Microbiol. Rev. 53 (2), 242–255.

Hudon, M.; Le Roux, E. & Harcourt, P. (1987). Agricult. Zool. Rev. 2, 1–44.

Hull & Howell (1987). Virology 86, 482–493.

Knowles, B. H. & Ellar, D. J. (1987). Biochim. Biophys. Acta 924, 509–518.

Lereclus, D.; Vallade, M.; Chaufaux, J.; Arantes, C. & Ralbaud, S. (1992). Bio/Technology 10, 418

Macintosh, S.C.; Stone, T. B.; Sims, S. R.; Hunst, P. L.; Greenplate, J. T.; Martone, P. G.; Perlak, F. J.; Fischhoff, D.A. & Fuchs, R. L. (1990). J. Inv. Pathol. 56, 258–266.

Munson, P. & Rodbard, D. (1980). LIGAND: a versatile computerized approach for characterizing of ligand-binding systems. Anal. Bioch. 107, 220–239.

Murray, E. E.; Rocheleau, T.; Eberle, M.; Stock, C.; Sekar, V. & Adang, M. (1991). Plant Mol. Biol. 16, 1035–1050.

Obukowicz, M. G.; Perlack, F. J.; Kusano-Kretzmer, K.; Meyer, E. J. & Watrud, L. S. (1986). Gene 45, 327–331.

Peferoen, M. (1991). Agro-Industry hi-tech 6, 5–9.

Perlak, F. J.; Fuchs, R. L.; Dean, D.A.; McPherson, S. L. & Fischhoff, D.A. (1991). Proc. Natl. Acad. Sci. USA 88, 3324–3328.

Poitout, S.; Bues, R. & Le Rumeur, C. (1972). Entomologia experimentalis et applicata 15, 341–350.

Reiss, B.; Sprengel, R.; Will, H. & Schaller, H. (1984). Gene 30, 217–223.

Stanssens, P.; Opsomer, C.; McKeown, Y.; Kramer, W.; Zabeau, M. & Fritz, H.-J. (1989). Nucl. Acids Res. 17, 4441–4454.

Stock, C. A.; McLoughlin, T. J.; Klein, J. A. & Adang, M. J. (1990). Can. J. Microbiol. 36, 879–884.

Turner, J. T.; Lampel, J. S.; Steaman, R. S.; Sundin, G. W.; Gunyuzlu, P. & Anderson, P. (1991). Appl. Environm. Micriobiol. 57, 3522–3528.

Vaeck, M.; Reynaerts, A.; Höfte, H.; Jansens, S.; De Beuckeleer, M.; Dean, C.; Zabeau, M.; Van Montagu, M. & Leemans, J. (1987). Nature 327, 33–37.

Van Rie, J.; Jansens, S.; Höfte, H.; Degheele, D. & Van Mellaert, H. (1989). Eur. J. Biochem. 186, 239–247.

Velten, J.; Velten, L.; Hain, R. & Schell, J. (1984). EMBO J. 3, 2723–2730.

Velten, J. & Schell, J. (1985). Nucl. Acids Res. 13, 6981–6998.

Visser, B.; van der Salm, T.; van den Brink, W & Folkers, G. (1988). Mol. Gen. Genet. 212, 219–224.

Wolfersberger, M.; Lüthy, P.; Maurer, A.; Parenti, P.; Sacchi, V.; Giordana, B. & Hanozet, G. (1987). Comp. Biochem. Physiol. 86(a), 301–308.

I claim:

1. A method to combat or control *Ostrinia nubilalis*, comprising the step of contacting said *Ostrinia nubilalis* with a CryIB protein comprising an amino acid sequence corresponding to amino acids 145 to 636 of the amino acid sequence of SEQ ID No. 1 or a variant thereof in which His at position 150 is replaced by Tyr, and a protein selected from the group of:

a CryIAb protein comprising an amino acid sequence corresponding to amino acids 29 to 607 of the amino acid sequence of SEQ ID No. 2 or variant thereof including at least one mutation selected from the group in which Asp at position 542 is replaced by His, Thr at position 568 is replaced by His, Val at position 569 is replaced by Leu, Gly at position 282 is replaced by Ala, Ser at position 283 is replaced by Leu, Ala at position 450 is replaced by Pro, Phe at position 537 is replaced by Leu and Pro at position 545 is replaced by Ile, and a CryIAc protein comprising an amino acid sequence corresponding to amino acids 1 to 609 of the amino acid sequence of SEQ ID No. 3 or variant thereof including at least one mutation selected from the group in which Phe at position 148 is replaced by Leu, Leu at position 366 is replaced by Phe, Phe at position 440 is deleted and Asn at position 442 is replaced by Ser.

2. The method according to claim 1, wherein the variant of the CryIAb protein is a variant in which Asp, Thr, and Val, respectively at positions 542, 568 and 569, are replaced by His, His and Leu; a variant in which Gly and Ser, respectively at positions 282 and 283, are replaced by Ala and Leu or a variant in which Ala, Phe and Pro, respectively at positions 450, 537 and 545, are replaced by Pro, Leu and Ile, and wherein in the variant of the CryIAc protein, Phe at position 148 is replaced by Leu, Leu at position 366 is replaced by Phe, Phe at position 440 is deleted and Asn at position 442 is replaced by Ser.

3. The method according to claim 1, wherein said contacting step is carried out with a microorganism transformed with at least one DNA sequence or a group of DNA sequences encoding said proteins.

4. The method according to claim 1, wherein said contacting step is carried out with a plant, stably transformed with at least one DNA sequence or group of DNA sequences encoding said proteins.

5. The method according to claim 4, wherein said plant is corn.

6. A plant infestable by *Ostrinia nubilalis* and which is protected from this insect by being stably transformed with at least one DNA fragment or group of DNA fragments encoding the group of proteins of claim 1.

7. A plant according to claim 6, wherein said plant is a corn plant.

8. The method according to claim 2, wherein said contacting step is carried out with a microorganism transformed with at least one DNA sequence or a group of DNA sequences encoding said protein or group of proteins.

9. The method according to claim 2, wherein said contacting step is carried out with a plant, stably transformed with at least one DNA sequence or group of DNA sequences encoding said proteins.

10. The method according to claim 9, wherein said plant is a corn plant.

11. A plant infestable by *Ostrinia nubilalis* and which is protected from this insect by being stably transformed with at least one DNA fragment or group of DNA fragments encoding the group of proteins of claim 2.

12. A plant according to claim 11, wherein said plant is a corn plant.

13. A plant infestable by *Ostrinia nubilalis* and which is protected from this insect by being stably transformed with a group of DNA sequences encoding a group of proteins, said group of proteins comprising the CryIB protein comprising the amino acid sequence of SEQ ID No. 1 or a variant thereof in which His at position 150 is replaced by Tyr, and a protein selected from the group of:

a CryIAb protein comprising the amino acid sequence of SEQ ID No. 2 or variant thereof including at least one mutation selected from the group in which Asp at position 542 is replaced by His, Thr at position 568 is replaced by His, Val at position 569 is replaced by Leu, Gly at position 282 is replaced by Ala, Ser at position 283 is replaced by Leu, Ala at position 450 is replaced by Pro, Phe at position 537 is replaced by Leu and Pro at position 545 is replaced by Ile, and a CryIAc protein comprising the amino acid sequence of SEQ ID No. 3 or variant thereof including at least one mutation selected from the group in which Phe at position 148 is replaced by Leu, Leu at position 366 is replaced by Phe, Phe at position 440 is deleted and Asn at position 442 is replaced by Ser.

* * * * *